(12) United States Patent
Kwon et al.

(10) Patent No.: US 9,709,515 B2
(45) Date of Patent: Jul. 18, 2017

(54) DEVICE AND METHOD FOR DIAGNOSING CRACKS IN A SOLIDIFIED SHELL IN A MOLD

(71) Applicant: Hyundai Steel Company, Incheon (KR)

(72) Inventors: Hyo Joong Kwon, Chuncheongnam-Do (KR); Yong Hee Kim, Daegu (KR); Hong Kil Moon, Chuncheongnam-Do (KR); Ju Tae Choi, Seoul (KR); Tae Jun Ha, Chungcheongnam-Do (KR)

(73) Assignee: Hyundai Steel Company, Dong-gu (KR)

( * ) Notice: Subject to any disclaimer, the term of this patent is extended or adjusted under 35 U.S.C. 154(b) by 385 days.

(21) Appl. No.: 13/852,335

(22) Filed: Mar. 28, 2013

(65) Prior Publication Data

US 2013/0211738 A1      Aug. 15, 2013

Related U.S. Application Data

(63) Continuation of application No. PCT/KR2011/006440, filed on Aug. 31, 2011.

(30) Foreign Application Priority Data

| Sep. 29, 2010 | (KR) | .................. 10-2010-0094486 |
| Sep. 29, 2010 | (KR) | .................. 10-2010-0094490 |
| Oct. 28, 2010 | (KR) | .................. 10-2010-0105685 |
| Oct. 28, 2010 | (KR) | .................. 10-2010-0105687 |
| Oct. 28, 2010 | (KR) | .................. 10-2010-0105689 |
| Nov. 29, 2010 | (KR) | .................. 10-2010-0119458 |

(51) Int. Cl.
| G01N 25/72 | (2006.01) |
| B22D 2/00 | (2006.01) |
| B22D 11/16 | (2006.01) |

(52) U.S. Cl.
CPC ............. *G01N 25/72* (2013.01); *B22D 2/006* (2013.01); *B22D 11/16* (2013.01)

(58) Field of Classification Search
CPC ..................................................... G01N 25/72
See application file for complete search history.

(56) References Cited

U.S. PATENT DOCUMENTS 4,774,998 A * 10/1988 Matsushita et al. .......... 164/453
4,949,777 A *  8/1990 Itoyama et al. .............. 164/453
5,904,202 A *  5/1999 Adamy ...................... 164/151.5

* cited by examiner

*Primary Examiner* — Manuel Rivera Vargas
(74) *Attorney, Agent, or Firm* — Locke Lord LLP; Howard M. Gitten

(57) ABSTRACT

The present invention relates to a system and method for diagnosing cracking in a solidified shell in a mold, in which whether longitudinal cracking has occurred in the solidified shell can be diagnosed in real time by using a variation in temperature of the solidified shell in the mold during a continuous casting process. The system comprises: a plurality of temperature sensors arranged in a matrix form in a mold, wherein the plurality of temperature sensors are divided into a first group and a second group based on where cracking occurs; and a processor configured to: calculate a temperature difference between the temperature of the first group and the temperature of the second group from the temperatures detected by the plurality of temperature sensors; and determine, using the calculated temperature difference, whether cracking has occurred in a solidified shell discharged from the mold.

8 Claims, 43 Drawing Sheets distribution of temperature at
various position of mold

DEVICE AND METHOD FOR DIAGNOSING CRACKS IN A SOLIDIFIED SHELL IN A MOLD

CROSS-REFERENCE TO RELATED APPLICATION

This is a continuation of International Application No. PCT/KR2011/006440 filed on Aug. 31, 2011, which claims priority to Korean Application No. 10-2010-0094486 filed on Sep. 29, 2010, Korean Application No. 10-2010-0094490 filed on Sep. 29, 2010, Korean Application No. 10-2010-0105685 filed on Oct. 28, 2010, Korean Application No. 10-2010-0105687 filed on Oct. 28, 2010, Korean Application No. 10-2010-0105689 filed on Oct. 28, 2010, and Korean Application No. 10-2010-0119458 filed on Nov. 29, 2010, which applications are incorporated herein by reference.

TECHNICAL FIELD

The present invention relates to a system and method for diagnosing cracking in a solidified shell in a mold during a continuous casting process.

BACKGROUND ART

Generally, a continuous casting machine is a system that produces cast steel having a specific size by supplying molten steel, produced in a steel-making furnace, to a continuous casting mold through a ladle unit and a tundish.

The continuous casting machine comprises a ladle unit for storing molten steel, a tundish, a continuous casting mold for cooling the molten steel discharged from the tundish to form continuously cast steel having a specific shape, and a plurality of pinch rolls connected to the mold and serving to move the continuously cast steel formed in the mold.

In other words, molten steel discharged from the ladle unit and the tundish is formed into continuously cast steel having a specific width and shape in the mold, and the continuously cast steel is transferred through the pinch rolls and cut by a cutter into slabs, blooms or billets having a specific shape.

SUMMARY

It is an object of the present invention to provide a system and method for diagnosing cracking in a solidified shell in a mold, in which whether longitudinal cracking has occurred in the solidified shell can be diagnosed in real time by using a variation in temperature of the solidified shell in the mold during a continuous casting process.

The objects of the present invention are not limited to the above-mentioned objects, and other objects of the present invention will be clearly understood by those skilled in the art to which the present invention pertains.

In order to accomplish the above objects, in one aspect, the present invention provides a system for diagnosing cracking in a solidified shell in a mold, the system comprising: a plurality of temperature sensors arranged in a matrix form in a mold, wherein the plurality of temperature sensors are divided into a first group and a second group based on where cracking occurs; and a processor configured to: calculate a temperature difference between the temperature of the first group and the temperature of the second group from the temperatures detected by the plurality of temperature sensors; and determine, using the calculated temperature difference, whether cracking has occurred in a solidified shell discharged from the mold.

The first group may comprise at least one temperature sensor disposed where no cracking occurs, and the second group comprises at least one temperature sensor disposed where cracking occurs.

In the system of the present invention, the processor may further be configured to: compare the calculated temperature difference with a set reference value to determine whether cracking has occurred in the solidified shell.

The temperature sensors in the first group may be disposed on both edges of the mold, and the temperature sensors in the second group may be disposed in a central portion of the mold, at each side of the central vertical line of the mold, which is an area corresponding to 15% or less of the width of the mold.

In the system of the present invention, the processor may further be configured to: determine whether cracking has occurred in the solidified shell using the temperature difference between an average temperature value of the first group and an average temperature value of the second group.

In the system of the present invention, the processor may further be configured to: determine whether cracking has occurred in the solidified shell using the temperature difference between an average temperature value of the first group and an average temperature value of temperature sensors other than any one of the temperature sensors of the second group.

In the system of the present invention, wherein the processor may further be configured to: extract a maximum temperature difference between an average temperature of the first group and an average temperature of each row of the second group; and determine whether cracking has occurred in the solidified shell using the extracted maximum temperature difference.

In the system of the present invention, the processor may further be configured to: calculate an average temperature of the first group and an average of each row of the second group; extract a maximum temperature difference and a minimum temperature difference between the calculated average temperature of the first group and the calculated average temperature of each row of the second group; and determine whether cracking has occurred in the solidified shell using the extracted maximum temperature difference and minimum temperature difference.

In another aspect, the present invention provides a method for diagnosing cracking in a solidified shell in a mold, the method comprising: detecting, by a processor, a mold temperature for each line of a matrix having a plurality of temperature sensors; extracting, by the processor, from the detected mold temperatures a temperature acquired from the temperature sensors in a first region of the mold where no cracking occurs and a temperature acquired from the temperature sensors in a second region of the mold where cracking occurs; calculating, by the processor, a temperature difference between the temperature of the first region and the temperature of the second region, and determining, by the processor, whether cracking has occurred in a solidified shell which is discharged from the mold using the calculated temperature difference.

The temperature of the first region of the mold may an average temperature value, and the temperature of the second region of the mold may be a minimum temperature value or an average temperature value.

Determining whether cracking has occurred in a solidified shell may include comparing, by the processor, the average value of repeatedly acquired temperature differences with a preset reference value to determine whether cracking has occurred in the solidified shell.

In still another aspect, the present invention provides method for diagnosing cracking in a solidified shell in a mold, the method comprising: detecting, by a processor, a mold temperature for each line of a matrix of a plurality of temperature sensors; extracting, by the processor, a maximum temperature and a minimum temperature for each line of the matrix from the detected mold temperatures, calculating, by the processor, a temperature difference between the maximum temperature and the minimum temperature; repeatedly acquiring, by the processor, the temperature difference at least once for a predetermined amount of time; and calculating, by the processor, an average value of the acquired temperature differences; and determining, by the processor, whether cracking has occurred in a solidified shell which is discharged from the mold using the calculated average value of the temperature differences.

Determining whether cracking has occurred in the solidified shell may further includes: repeatedly acquiring, by the processor, the average value of the temperature differences for a predetermined amount of time; extracting, by the processor, a maximum average value and a minimum average value from the acquired average values; calculating, by the processor, a difference between the extracted maximum average value and minimum average value, and comparing, by the processor, the calculated difference with a preset reference value to determine whether cracking has occurred in the solidified shell, for each line of the matrix.

In yet another aspect, the present invention provides a system for diagnosing cracking in a solidified shell in a mold, the system comprising: a temperature sensor unit configured to detect the temperature of the mold using a plurality of temperature sensors arranged in a central portion of the mold, in which cracking occurs; and a processor configured to: collect the temperature of the mold using the plurality of temperature sensors for a predetermined amount of time; calculate from the collected mold temperatures, a temperature difference between a maximum temperature measured before the temperature of each temperature sensor decreases and a minimum temperature measured after the temperature has decreased; and determine whether cracking has occurred in a solidified shell discharged from the mold using the calculated temperature difference.

The processor is further configured to: compare the maximum temperature difference among the calculated temperature differences with a preset reference value to determine whether cracking has occurred in the solidified shell.

The processor is further configured to: store the maximum temperature and the minimum temperature of each temperature sensor when the calculated temperature difference is greater than the reference value; and determine whether cracking has occurred in the solidified shell using the temperature of each temperature sensor disposed in a same row of the matrix.

The processor is further configured to: calculate an interline movement time of the temperature difference using the temperature of the temperature sensors disposed in the same row of the matrix; and determine whether the calculated movement time is within a set reference condition range to determine whether cracking has occurred in the solidified shell.

In still another aspect, the present invention provides a method for diagnosing cracking in a solidified shell in a mold, the method comprising: periodically collecting, by a processor, a mold temperature using a plurality of temperature sensors arranged in a matrix form in the mold; calculating, by the processor, a temperature difference between a maximum temperature before the temperature of each temperature sensor decreases and a minimum temperature after the temperature of each temperature sensor has decreased, using the collected mold temperatures after a predetermined amount of time; and determine, by the processor, whether cracking has occurred in the solidified shell using the calculated temperature difference.

Determining whether cracking has occurred in the solidified shell further includes: extracting, by the processor, the maximum temperature difference for each temperature sensor from the calculated temperature differences; and comparing, by the processor, the extracted maximum temperature difference for each temperature sensor with a preset reference value to determine whether cracking has occurred in a solidified shell corresponding to each temperature sensor.

Determining whether cracking has occurred in the solidified shell further includes: comparing, by the processor, the calculated temperature difference with the set reference value; storing, by the processor, a maximum temperature and a minimum temperature of the temperature sensors when the temperature difference is greater than the reference value; calculating, by the processor, an interline movement time of the temperature difference using the temperature of the temperature sensors, and determining whether the calculated movement time is within a set reference condition range to determine whether cracking has occurred in the solidified shell.

According to the present invention, longitudinal cracking is diagnosed based on the variation in temperature of a solidified shell that is produced in a continuous casting process, so that only the surface of a slab in which longitudinal cracks have occurred can be scarfed, thus reducing the cost for correcting slabs.

In addition, according to the present invention, when longitudinal cracking has occurred in a slab, operating conditions are changed, thereby reducing the failure rate of a slab that is produced in a continuous casting process.

DESCRIPTION OF THE REFERENCE NUMERALS IN THE DRAWINGS

Figure 1:
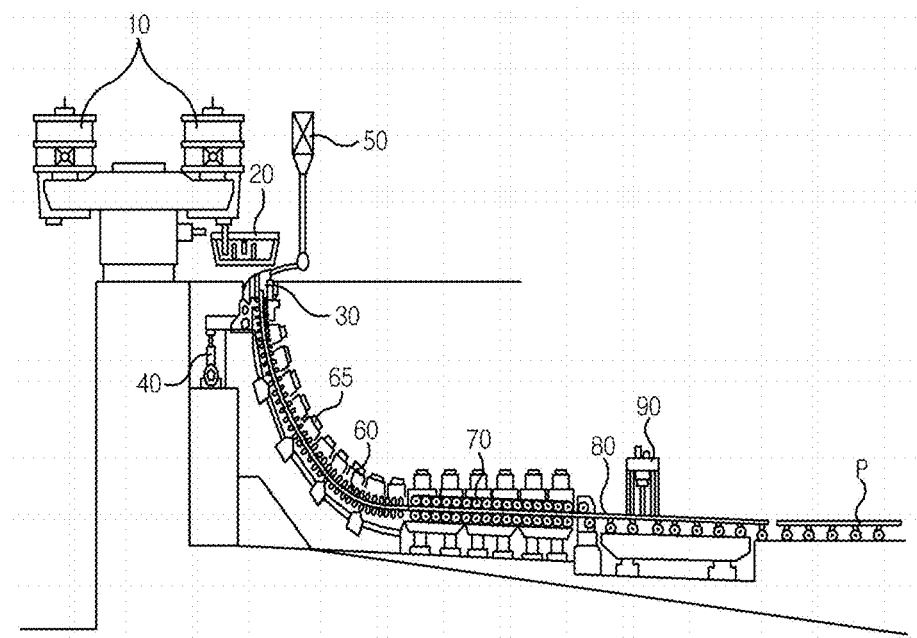
FIG. 1 is a side view showing a continuous casting machine related to an embodiment of the present invention.

10: ladle; 15: shroud nozzle;
20: tundish; 25: submerged entry nozzle;
30: mold; 31: long side of mold;
35: short side of mold; 40: oscillator;
50: powder feeder; 51: powder layer;
52: liquid flow layer; 53: lubricating layer;
60: support rolls; 65: spray;
70: pinch rolls; 80: continuously cast steel;
81: solidified shell; 82: non-solidified molten steel;
83: end; 85: solidification ending point;
87: oscillation mark; 88: bulging region;
90: cutter; 91: cutting position;
100: crack diagnosis system; 101: first group;
102: second group; 110: temperature sensing unit;
111: temperature sensors of first group;
112: temperature sensors of second group
130: memory; 150: display unit;
170: input unit; 190: processor;
191: difference calculation unit;
191-1: average-temperature calculation unit;
191-2: temperature collection unit;
193: average-difference calculation unit;
193-1: difference extraction unit;
193-2: differentiation calculation unit;
193-3: reference-value comparison unit;
195: crack determination unit.

DETAILED DESCRIPTION

Hereinafter, preferred embodiments of the present invention will be described in further detail with reference to the accompanying drawings. In the following description, the same elements will be indicated by the same reference numerals wherever possible, even if they are shown in different drawings. Further, the detailed description of known functions and configurations will be omitted when it may obscure the subject matter of the present invention.

FIG. 1 is a side view of a continuous casting machine related to one embodiment of the present invention.

Referring to FIG. 1, the continuous casting machine may comprise a tundish 20, a mold 30, secondary cooling zones 60 and 65, pinch rolls 70, and a cutter 90.

The tundish 20 is a container that receives molten steel from a ladle unit 10 and supplies the molten steel to the mold 30. The ladle unit 10 is composed of a pair of ladles: a first ladle 11 and a second ladle 12. The ladles 11 and 12 alternately receive the molten steel and alternately supply the molten steel to the tundish 20. In the tundish 20, the control of feed rate of the molten steel into the mold 30, the distribution of the molten steel to each mold 30, the storage of the molten steel, the separation of slag and non-metal inclusions, etc., are performed The mold 30 is generally a water-cooled mold made of copper, in which the molten steel is primarily cooled. The mold 30 has a structure in which a pair of opposite faces are spaced apart from each other and provide a cavity in which the molten steel is received. When a slab is to be produced, the mold 30 comprises a pair of long walls and a pair of short walls connecting the long walls with each other. Herein, the long walls have a smaller area than the short walls. The walls (mainly short walls) of the mold 30 are tapered to each other such that they are distant from each other or close to each other. This taper is set in order to compensate for shrinkage caused by the solidification of the molten steel (M) in the mold 30. The degree of solidification of the molten steel (M) varies depending on the carbon content of the steel, the type of powder (fast cooling type or slow cooling type), casting velocity, etc.

The mold 30 functions to form a strong solidified shell (see FIG. 2) such that a continuously cast steel drawn from the mold maintains its shape and non-solidified molten steel does not flow out. Water cooling structures for use in the mold include a structure employing a copper tube, a structure having a water cooling groove formed in a copper block, and a structure employing a copper tube assembly having a water cooling groove.

The mold 30 is oscillated by an oscillator 40 in order to prevent molten steel from adhering to the wall surface of the mold. A lubricant is used to reduce the friction between the mold 30 and the continuously cast steel during oscillation. Examples of the lubricant include rapeseed oil, which is sprayed, and powder, which is added to the surface of molten steel in the mold 30. The powder is added to molten steel in the mold 30 to form slag and functions to provide lubrication between the mold 30 and the continuously cast steel and to prevent oxidation and nitrification of molten steel in the mold 30, and also to keep the molten steel warm. In addition, it functions to absorb non-metal inclusions on the surface of molten steel. A powder feeder 50 is provided in order to introduce the powder into the mold 30. The portion of the powder feeder 50 that discharges the powder is directed toward the inlet of the mold 30.

The secondary cooling zones 60 and 65 serve to additionally cool the molten steel primarily cooled in the mold 30. The primarily cooled molten steel is cooled directly by water spray means 65 while it is supported by support rolls 60 such that the solidified shell is not deformed.

The solidification of the continuously cast steel is mostly achieved by the secondary cooling. A drawing device adopts a multi-drive method that uses several sets of pinch rolls 70 so as to draw the continuously cast steel without sliding. The pinch rolls 70 pull the solidified end of the molten steel in the casting direction so that the molten steel that passed through the mold 30 can continuously move in the casting direction.

The cutter 90 is provided so as to cut the continuously cast steel into a constant size. The cutter 90 may be a gas torch or a hydraulic shear.

Figure 2:
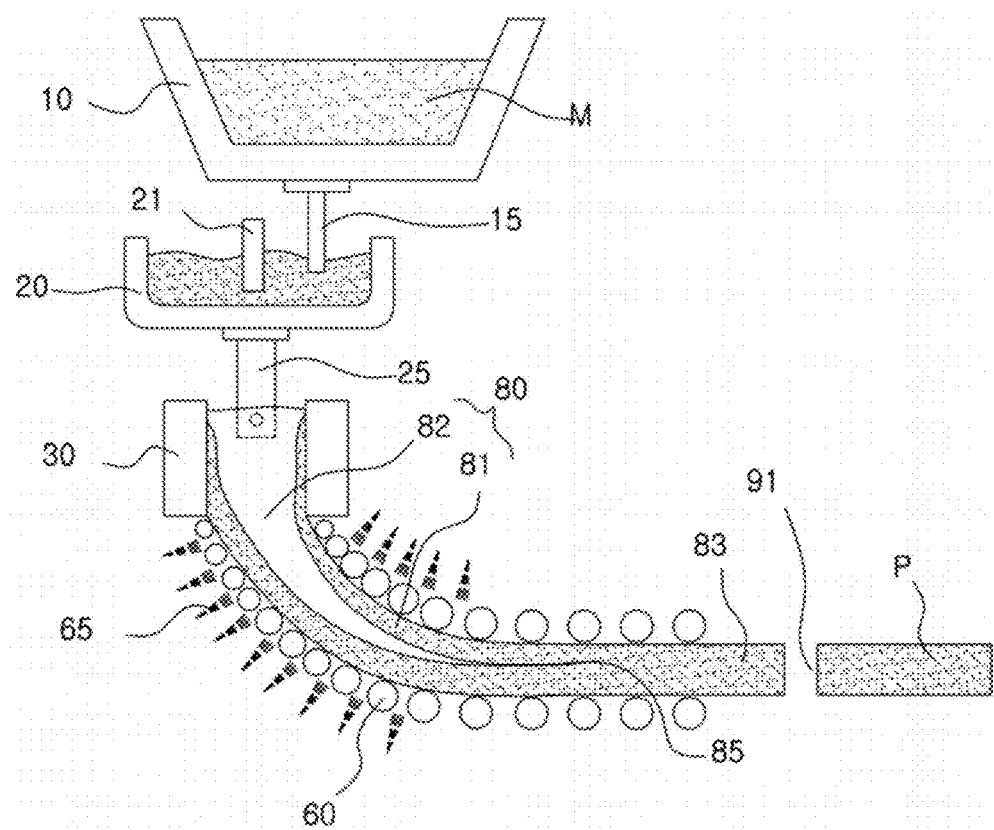
FIG. 2 is a conceptual view explaining the continuous casting machine of FIG. 1 with respect to the flow of molten steel (M).

FIG. 2 is a conceptual view explaining the continuous casting machine of FIG. 1 with respect to the flow of molten steel M.

Referring to FIG. 2, molten steel (M) in the ladle unit 10 flows into the tundish 20. To perform this flow process, the ladle unit 10 is provided with a shroud nozzle 15 extending toward the tundish 20. The shroud nozzle 15 extends to be submerged into the molten steel (M) in the tundish 20 so as to prevent the molten steel (M) from being oxidized and nitrified by exposure to air. Exposure of the molten steel (M) to air due to breakage of the shroud nozzle 15 is called "open casting".

The molten steel (M) in the tundish 20 flows into the mold 30 through a submerged entry nozzle 25 extending into the mold 30. The submerged entry nozzle 25 is disposed at the center of the mold 30 so that the flows of the molten steel (M) discharged from both outlets of the submerged entry nozzle 25 are symmetrical. The commencement of discharge of the molten steel (M) from the submerged entry nozzle 25, the discharge speed and the cessation of the discharge are determined by a stopper 21 that is disposed in the tundish 20 so as to correspond to the submerged entry nozzle 25. Specifically, the stopper 21 can move vertically along the same line as the submerged entry nozzle 25 so as to open and close the inlet of the submerged entry nozzle 25. The flow of the molten steel (M) through the submerged entry nozzle 25 can be controlled by a slide gate method as opposed to a stopper method. In the slide gate method, a plate slides horizontally in the tundish 20 to control the discharge flow rate of the molten steel (M) through the submerged entry nozzle 25.

The molten steel (M) in the mold 30 starts to solidify from the peripheral portion of the molten steel (M), which comes into contact with the inner walls of the mold 30. This is because the peripheral portion of the molten steel (M) is more likely to lose heat by the mold 30 being cooled by water compared to the central portion. Because the peripheral portion is solidified first, the downward portion of the continuously cast steel 80 in the casting direction is in a form in which the non-solidified molten steel 82 is surrounded by the solidified shell 81.

As the pinch rolls 70 (FIG. 1) pull the end 83 of the completely solidified, continuously cast steel 80, the non-solidified molten steel 82 together with the solidified shell 81 moves in the casting direction. In the movement process, the non-solidified molten steel 82 is cooled by spray means 65 that spray cooling water. This gradually reduces the thickness of the non-solidified molten steel 82 in the continuously cast steel 80. When the continuously cast steel reaches a point 85, the entire thickness thereof is composed of the solidified shell 81. The completely solidified continuously cast steel 80 is then cut into specific sizes in a cutting place 91 to form pieces P such as slabs.

Figure 3:
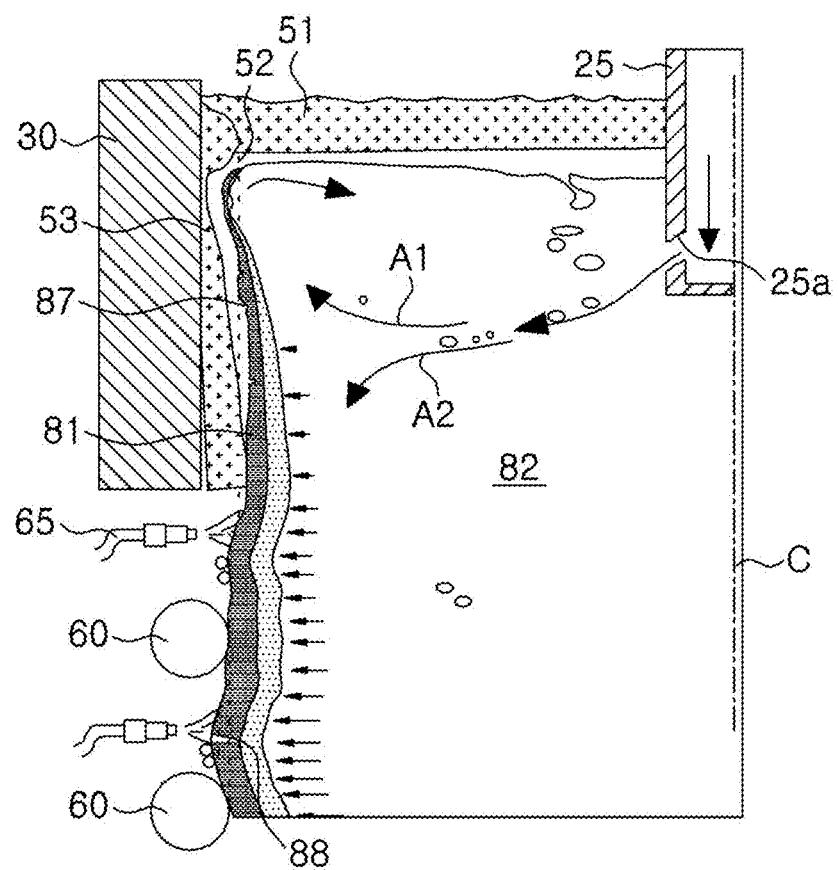
FIG. 3 is a conceptual view showing the distribution of molten steel (M) in the mold of FIG. 2 and a portion adjacent thereto.

The shape of molten steel (M) in the mold 30 and the portion coming into contact therewith will now be described with reference to FIG. 3. FIG. 3 is a conceptual view showing the distribution of molten steel (M) in the mold 30 and the portion coming into contact therewith.

Referring to FIG. 3, at the end of the submerged entry nozzle 25, a pair of discharge holes are formed on both sides of a centerline C. Assuming that the shape of each of the mold 30 and the submerged entry nozzle 25 is symmetrical with respect to the centerline C, only the left side of the shape is shown in FIG. 3.

The molten steel (M) discharged from the discharge hole 25a together with argon gas (Ar) flows in an upward direction A1 and a downward direction A2.

In the upper portion of the mold 30, a powder layer 51 is formed of powder supplied from the powder feeder 50 (see FIG. 1). The powder layer 51 may comprise a layer of non-sintered powder and a layer of powder sintered by the heat of the molten steel (M) (the sintered powder layer is formed closer to the non-solidified molten steel 82). A slag layer or a liquid flow layer 52 formed of powder melted by the molten steel (M) is present under the powder layer 51. The liquid flow layer 52 serves to maintain the temperature of the molten steel (M) in the mold 30 and prevent the infiltration of foreign matter into the mold 30. A portion of the powder layer 51 is solidified on the wall surface of the mold 30 to form a lubricating layer 53. The lubricating layer 53 functions to prevent the solidified shell 81 from sticking to the mold 30. The thickness of the solidified shell 81 becomes thicker in the casting thickness. The portion of the solidified shell 81, which is located in the mold 30, has a thin thickness, and an oscillation mark 87 may also be formed as a result of oscillation of the mold 30. The solidified shell 81 is supported by support rolls 60, and the thickness thereof becomes thicker by spray means 65 that spray water. The solidified shell 81 becomes gradually thicker and may have a bulging portion 88.

If the release of heat released from the mold 30 is non-uniform, the thickness of the central portion of the solidified shell 81 becomes thicker. The solidified shell 81 is non-uniformly solidified for various reasons, including a difference in the level of molten steel in the mold, intensive flow in the mold (development of turbulent or eddy flow), non-uniform introduction of powder into the mold, and the like.

Meanwhile, in the non-uniformly solidified shell 81, tension is applied to the non-uniformly solidified layer portion due to phase transformation and thermal shrinkage to cause an air gap between the mold 30 and the solidified shell 81, thus causing cracks in the solidified shell 81. Herein, the cracks can be formed on the surface and inside of the solidified shell 81.

Thus, the system for diagnosing cracks according to the present invention aims to diagnose whether cracks have occurred in the solidified shell 81 and to accurately extract the cracked slab in order to perform scarfing.

Figure 4:
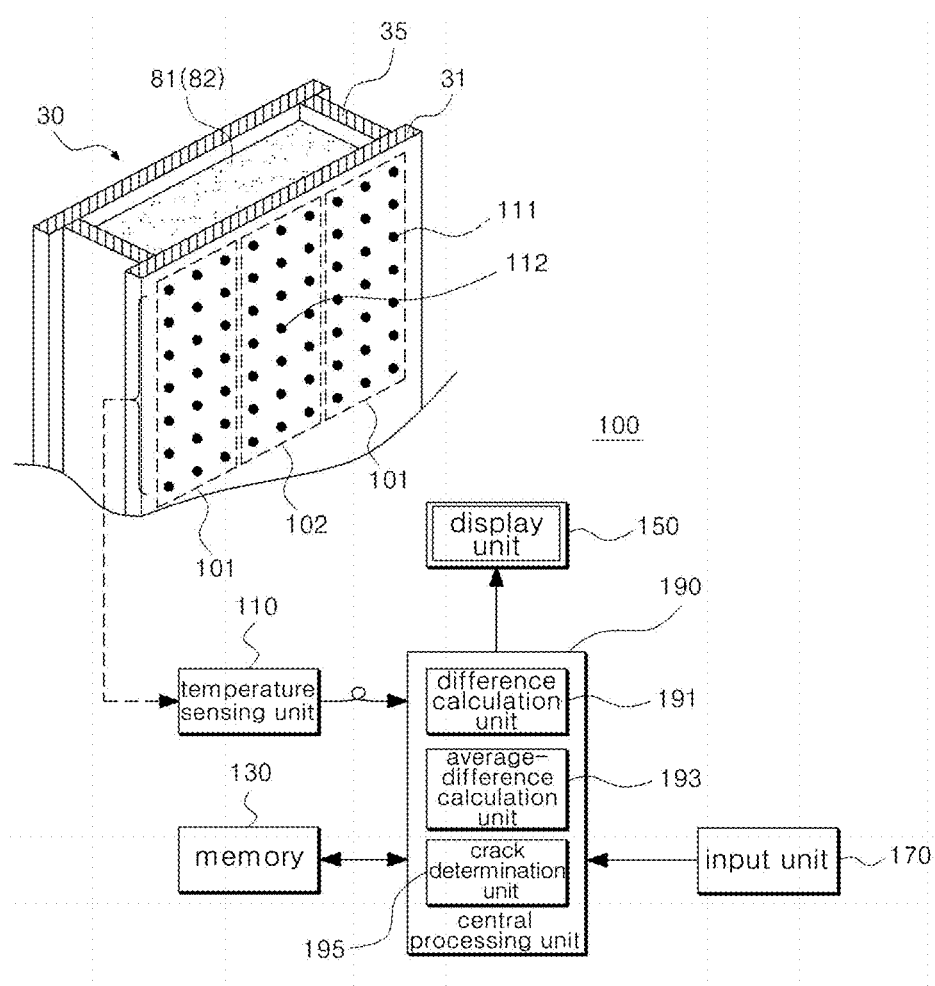
FIG. 4 shows a system for diagnosing cracking in a solidified shell in a mold according to a first embodiment of the present invention.

FIG. 4 shows a system for diagnosing cracks in a solidified shell in a mold according to a first embodiment of the present invention. As can be seen therein, a crack diagnosis system 100 comprises a temperature sensing unit 110, a memory 130, a display unit 150, an input unit 170 and a processor 190.

The temperature sensing unit 110 comprises a plurality of temperature sensors 111 and 112 arranged in a matrix form along the long side 31 of the mold 30. The plurality of temperature sensors 111 and 112 arranged in the mold 30 sense the temperature of the mold 30 in real time during a continuous casting process. The temperature of the mold 30 is regarded to be the same as the temperature of the solidified shell 81 present in the mold 30.

The temperature sensors 111 and 112 have identification information for identifying the respective regions arranged in the mold 30. Thus, when the temperature of the mold 30 is sensed by each of the temperature sensors 111 and 112, the temperature sensor 110 transmits the sensed temperature information 170.

Figure 5:
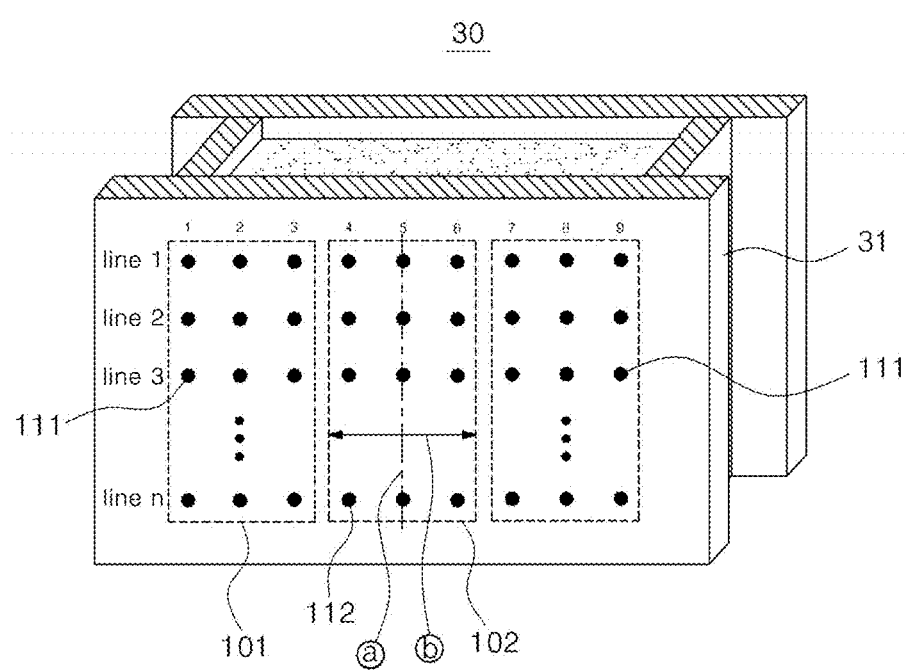
FIG. 5 shows temperature sensors arranged in the long side of a mold according to the present invention.

As shown in FIG. 5, the temperature sensors 111 and 112 of the temperature sensors 110 are arranged and embedded in the long side 31 of the mold in a matrix form. The temperature sensors 111 and 112 may be either of thermocouples and temperature sensors.

The plurality of temperature sensors 111 and 112 arranged in the mold 30 are divided into a first group 101 and a second group 102 with respect to a region in which cracks can occur. Generally, cracks occur in the central portion of the long side 31 of the mold. As shown in FIG. 4 or 5, the temperature sensors 112 belonging to the second group 102 are arranged in the central portion of the mold 30, and the temperature sensors 111 belonging to the first group 101 are arranged in both edges of the mold 30. The first group 101 includes at least one temperature sensor 111 disposed in a region in which no cracks occur, and the second group 102 includes at least one temperature sensor 112 disposed in a region in which cracks occur. The embodiment of the present invention illustrates that the first group 101 has six temperature sensors 111 per line and the second group has three temperature sensors 112 per line, but the number of the temperature sensors 111 and 112 can be changed as required.

The temperature sensors 112 belonging to the second group 102 are located at each of both sides of the central vertical line ⓐ the mold 30, which is an area corresponding to 15% or less of the width of the mold 30. In other words, the second group 102 is located in the central portion of the long side 31 of the mold, which is a region ⓑ corresponding to about 30% of the width of the long side 31.

Although FIG. 5 illustrates that the plurality of temperature sensors 111 and 112 are arranged throughout the long side 31 of the mold, they may also be selectively arranged at the upper, lower or central portion of the long side 31 of the mold. It should be noted that, when the temperature sensors 111 and 112 are arranged throughout the long side 31 of the mold, accuracy for crack detection can be improved.

The memory 130 stores a time period and unit time for detection of the temperature of the mold 30, a reference value for determining the occurrence of cracks, and various control programs.

The display unit 150 can display the differences in temperature between the first group 101 and the second group 102 and the average value of the temperature differences as a function of time. The display unit 150 can graphically display the differences in temperature.

The input unit 170 is configured such that it receives various operational commands or set values from the outside and transmits them to the processor 190.

The processor 190 acquires the average temperature value of the first group 101 and the minimum temperature value of the second group 102 for each line from the temperatures detected by the temperature sensing unit 110, and uses the difference between the acquired average temperature value and minimum temperature value to diagnose whether cracks have occurred in the solidified shell 81 discharged from the mold 30. Herein, the difference between the average temperature value and the minimum temperature value is determined for each line.

For example, when the temperature sensors 111 and 112 are arranged in a matrix of N (lines)×9 (rows) as shown in FIG. 5, the first group 101 is the temperature sensors 111 belonging to rows 1, 2, 3, 7, 8 and 9, and the second group 102 is the temperature sensors 112 belonging to rows 4, 5 and 6.

The processor 190 determines the average temperature value using the temperature information detected by the temperature sensors 111 disposed in rows 1, 2, 3, 7, 8 and 9 of the long side 31 of the mold, and extracts the minimum temperature value from the temperature information sensed by the temperature sensors 112 disposed in rows 4, 5 and 6. Then, the processor 190 calculates the difference in temperature by subtracting the minimum temperature value from the average temperature value and temporarily stores the calculated temperature difference together with the measurement time information in the memory 130.

The processor 190 can repeatedly acquire the average temperature value, the minimum temperature value and the temperature difference one or more times for a set time, and compares the average value of the repeatedly acquired temperature differences with a preset reference value. In this way, whether cracking has occurred in the solidified shell 81 is diagnosed for each line.

The processor 190 may comprise a difference calculation unit 191, an average-difference calculation unit 193 and a crack determination unit 195.

In the difference calculation unit 191, each of the average temperature value of the temperature sensors 111 belonging to the first group 101 and the minimum temperature value of the temperature sensors 112 belonging to the second group 102 is acquired for each line from the temperatures sensed by the temperature sensing unit 110, the difference between the acquired average temperature value and minimum temperature value is calculated. Of course, the difference calculation unit 191 can temporarily store the temperature difference, calculated from the periodically acquired average temperature value and minimum temperature value, together with the measurement time information in the memory 130.

In the average-difference calculation unit 193, temperature differences repeatedly acquired for a set time are read from the memory 130, and then the average value of temperature differences per set unit time is calculated.

In the crack determination unit 195, the average value of temperature differences calculated by the average-difference calculation unit 193 is compared with a preset reference value, and based on the comparison results, whether cracking has occurred in the solidified shell 81 is diagnosed for each line.

The average value of temperature differences calculated by the average-difference calculation unit 193 of the processor 190 may also be displayed on the display unit 150.

Meanwhile, the processor 190 acquires each of the average temperature value of the first group 101 and the minimum temperature value of the second group 102 for each line from the temperatures detected by the temperature sensing unit 110, and stores the temperature difference between the acquired average temperature value and minimum temperature value. Herein, the processor 190 may repeatedly acquire the average temperature value, the minimum temperature value and the temperature difference one or more times for a set time, and collect the average value of the repeatedly acquired temperature differences for a set elementary time. Thus, whether cracking has occurred in the solidified shell 81 may be diagnosed for each line by collecting the average difference value for an elementary time and comparing the maximum difference among the collected average difference values with a preset reference value.

In addition, the processor 190 can also diagnose whether cracking has occurred in the solidified shell, by repeatedly acquiring the average temperature value, the minimum temperature value and the temperature difference one or more times for a set time for each line, and comparing the maximum value among the average values of the repeatedly acquired temperature differences for each line with a preset reference value.

Figure 6:
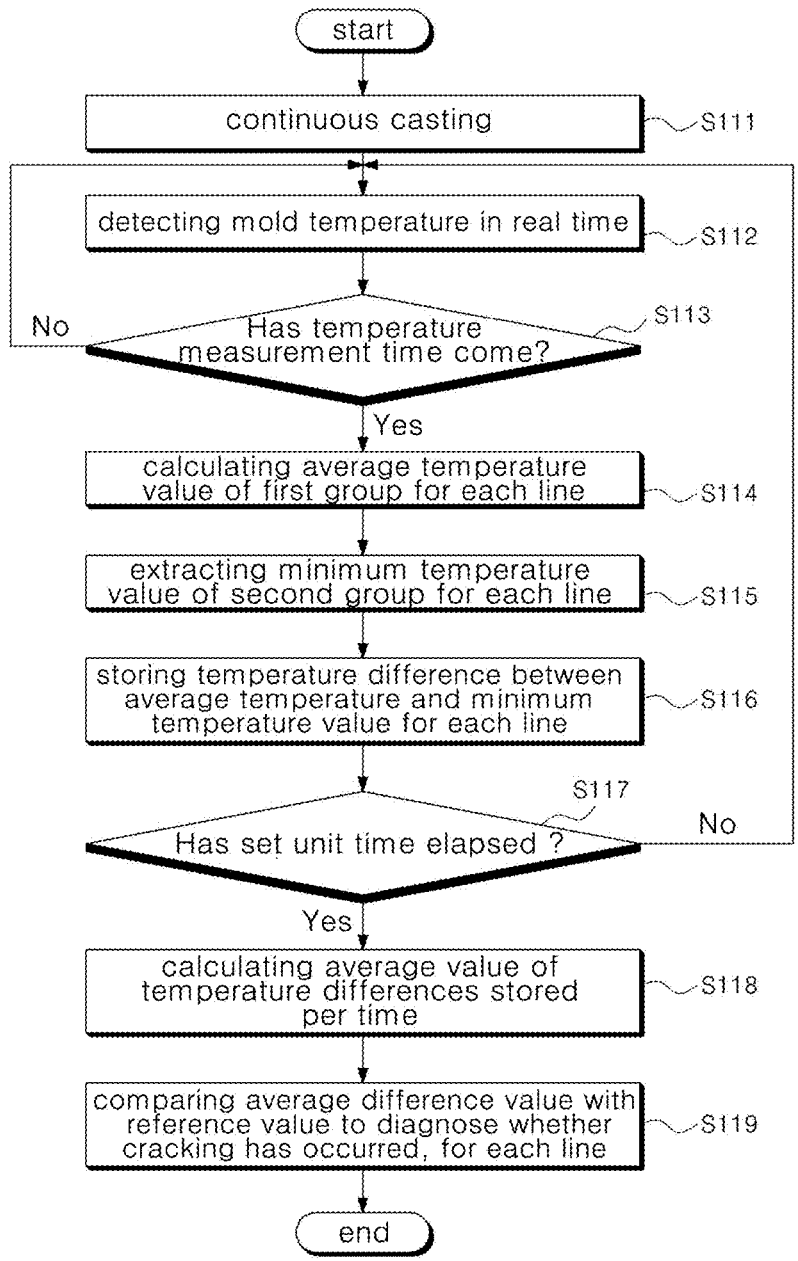
FIG. 6 is a flowchart showing a process for diagnosing cracking in a solidified shell according to one embodiment of the present invention.

FIG. 6 is a flowchart showing the process for diagnosing cracks in a solidified shell according to the embodiment of FIG. 4.

As shown in FIG. 6, during a continuous casting process, the temperature sensing unit 110 senses in real-time the temperatures of regions of the mold 30 in which the temperature sensors 111 and 112 are disposed, and transmits the sensed temperature to the processor 190 (S111 and S112). Herein, the temperature sensor unit 110 transmits the identification information of each of the temperature sensors 111 and 112 together with the temperature information to the processor 190. From the transmitted identification information, the processor 190 can determine whether the temperature information belongs to the first group 101 or the second group 102.

The plurality of temperature sensors 111 and 112 are divided into the first group 101 and the second group 102 with respect to a region in which cracks can occur. The first group 101 is disposed in both edges of the long side 31 of the mold, in which no cracks occur, and the second group is disposed at the central portion of the long side 31 of the mold, in which cracks occur.

Figure 7:
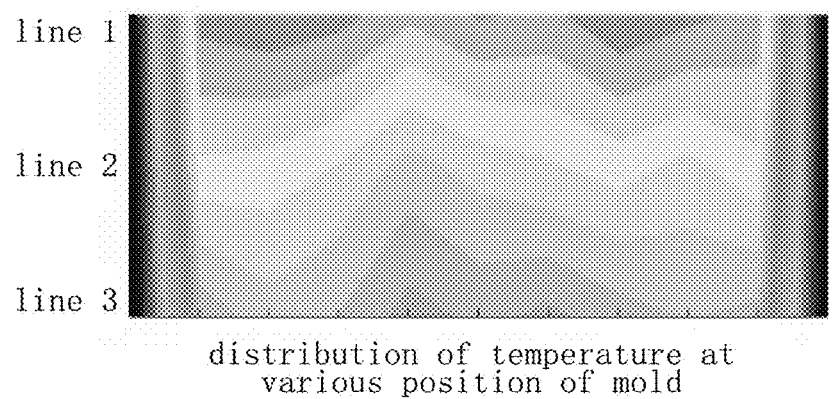
FIG. 7 shows the temperature of a solidified shell in a mold, measured according to the present invention.

FIG. 7 shows the temperatures of the mold at specific time points. Specifically, FIG. 7 shows the temperatures of the mold 30, detected by the temperature sensors 111 and 112 located in lines 1, 2 and 3, at specific time points.

As can be seen in FIG. 7, the temperature of the mold 30 varies depending on location, and particularly, the central portion of the mold 30 shows a significant change in temperature.

When the set temperature measurement time (T) is reached (S113), the processor 190 calculates the average temperature value of the first group 101 in any line using the temperature information of the temperature sensors 111 of the first group 101 which is present in a region in which no cracks occur (S114).

In addition, after calculating the average temperature value of the first group 101, the processor 190 extracts the minimum temperature value from the temperature information for the temperature sensors 112 of the second group 102 in any line, which is present in the region in which cracks occur (S115).

The processor 190 calculates the temperature difference by subtracting the minimum temperature value from the acquired average temperature value and temporarily stores the calculated temperature difference together with the measurement time information in a memory 130 (S116). Herein, the processor 190 may display the calculated temperature difference on the display unit 150 as a function of time.

Then, the processor 190 determines whether the set unit time (N, or the number of unit times) has elapsed (S117), and if the set unit time has not elapsed, the above steps (S114 to S116) are repeated to acquire the average temperature value, the minimum temperature value and the temperature difference again, and the acquired temperature difference together with the measurement time information is temporarily stored in the memory 130.

These steps are repeatedly performed for the set unit time (N). When the set unit time (N, or the number of unit times) has elapsed (S117), the processor 190 reads the repeatedly acquired temperature differences from the memory 130 to calculate the average value of the temperature differences (S118), and whether cracking has occurred in the solidified shell 81 is diagnosed for each line by comparing the calculated average difference value with a preset reference value (S119). Herein, the processor determines that cracks have occurred in the solidified shell 81 if the average value of the temperature differences is greater than the reference value.

Figure 8:
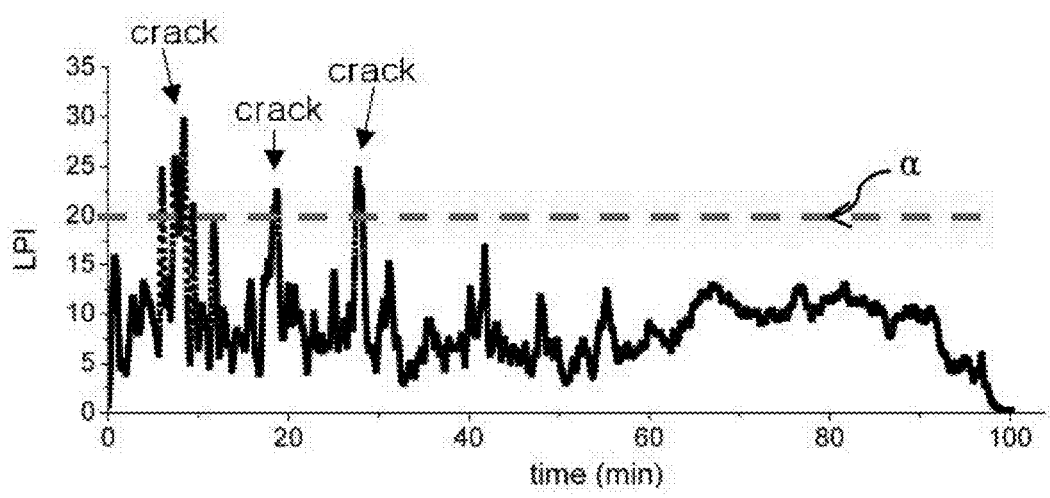
FIG. 8 is a graphic diagram showing the average value of the temperature differences, calculated in FIG. 6, as a function of time.

The processor 190 may also display the average difference value, calculated per set unit time (N) for any line, on the display unit 150 as a function of time as shown in FIG. 8.

In FIG. 8, the y-axis represents a longitudinal probability index (LPI) which is the average difference value calculated per unit time for any line, and the x-axis is the time axis.

As shown in FIG. 8, in the embodiment of the present invention, the reference value ($\alpha$) is set at 20, and if the average difference value (LPI) is greater than 20, the processor 190 determines that longitudinal cracks have occurred in the solidified shell 81 in the mold 30. Herein, the reference value ($\alpha$) may differ between the lines in which the temperature sensors 111 and 112 are disposed.

Figure 9:
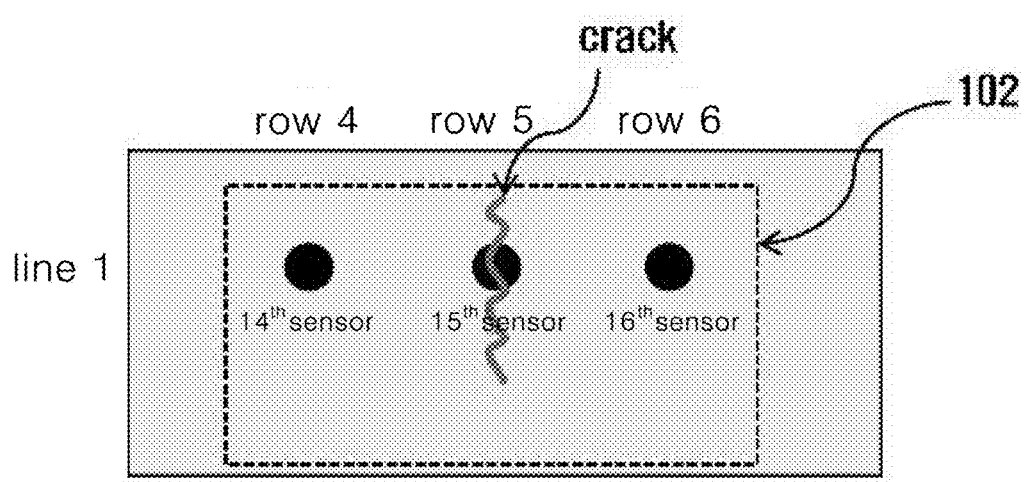
FIG. 9 shows cracking in a mold.

In other words, as shown in FIG. 9, if the average difference value (LPI) is greater than the reference value ($\alpha$), it is determined that longitudinal cracks have occurred at the central portion of the long side 31 of the mold, that is, the portion of the solidified shell 81 that corresponds to the second group 102. If cracks occur at the portion of the solidified shell 81 that corresponds to row 5 of line 1, the temperature of the mold 30 detected by a $15^{th}$ sensor will be lower than the temperatures of the mold 30 detected by a $14^{th}$ sensor and a $16^{th}$ sensor located at row 4 and row 6, respectively. The crack diagnosis algorithm according to the present invention shows relatively excellent crack diagnosis performance when cracks occur at portions corresponding to the temperature sensing sensors 112 of the second group 102.

Meanwhile, whether cracking has occurred in the solidified shell can also be diagnosed by comparing a preset reference value with the maximum value among the average values of the temperature differences for each line, repeatedly acquired in the steps (S112 to S118).

Figure 10:
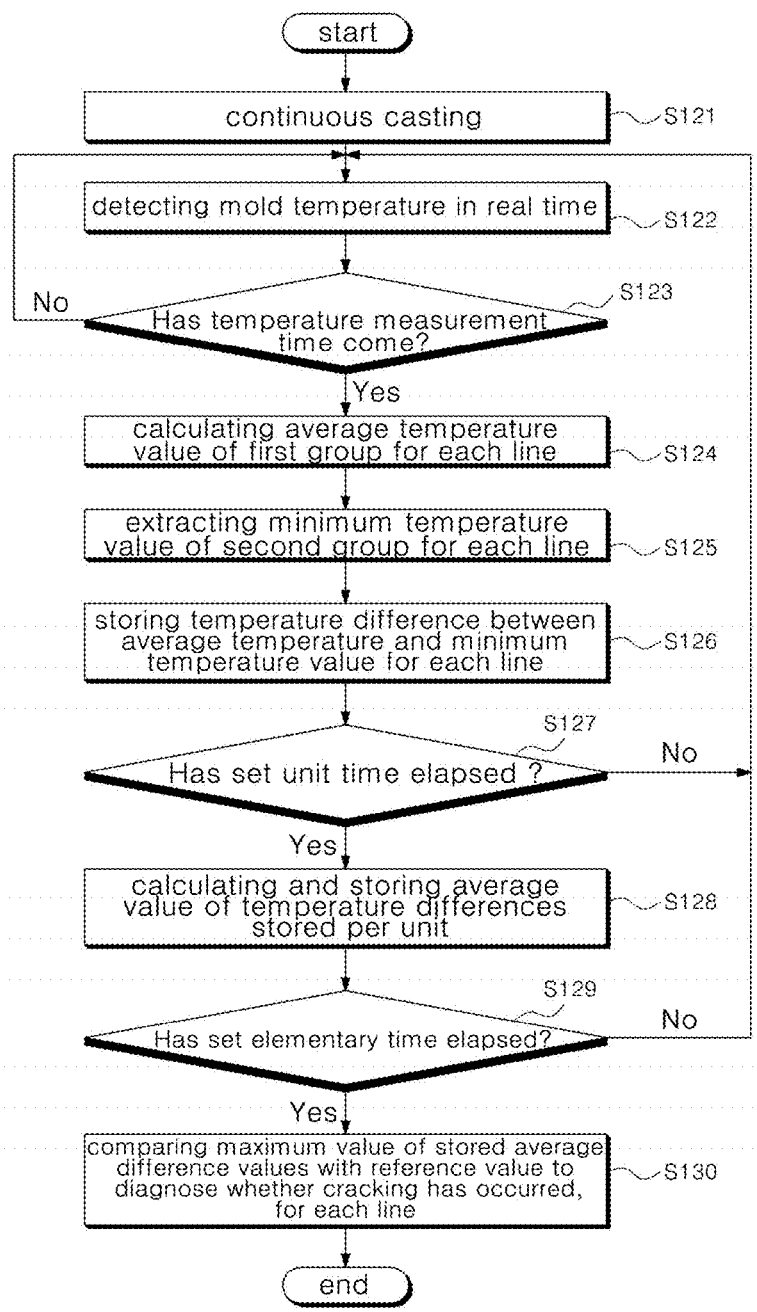
FIG. 10 is a flowchart showing a process for diagnosing cracking in a solidified shell according to another embodiment of FIG. 4.

FIG. 10 is a flowchart showing a process for diagnosing cracks in a solidified shell according to another embodiment of the present invention.

Referring to FIG. 10, during a continuous casting process, the temperature sensing unit 110 senses in real-time the temperatures of regions of the mold 30 in which the temperature sensors 111 and 112 are disposed, and the sensed temperature is transmitted to the processor 190 (S121 and S122).

The plurality of temperature sensors 111 and 112 are divided into the first group 101 and the second group 102 with respect to a region in which cracks can occur. The first group 101 is disposed in both edges of the long side 31 of the mold, in which no cracks occur, and the second group is disposed at the central portion of the long side 31 of the mold, in which cracks occur.

When the set temperature measurement time (T) is reached (S123), the processor 190 calculates the average temperature value of the first group 101 for each line using the temperature information of the temperature sensors 111 corresponding to the first group 101 present in the region in which no cracks occur (S124).

Also, the processor 190 calculates the average temperature value of the first group 101, and then for each line, it extracts the minimum temperature value from the temperature information of the temperature sensors 112 of the second group 102 present in the region in which cracks occur (S125).

The processor 190 calculates the temperature difference by subtracting the minimum temperature value from the average temperature value acquired for each line, and temporarily stores the calculated temperature together with the measurement time information in the memory 130 (S126). Herein, the processor 190 may also display the calculated temperature difference as a function of time on the display unit 150.

Then, the processor 190 determines whether the set unit time (N, or the number of unit times) has elapsed (S127), and if the set unit time has not elapsed, the above steps (S122 to 5126) are repeated to acquire the average temperature value, the minimum temperature value and the temperature difference again, and the acquired temperature difference together with the measurement time information is temporarily stored in the memory 130.

This process is repeatedly performed for the set unit time (N). If the set unit time (N, or the number of unit times) has elapsed (S127), the processor 190 reads the repeatedly acquired temperature differences from the memory to calculate the average value of the temperature differences and temporarily stores the calculated average difference value in the memory 130 (S128).

Figure 11:
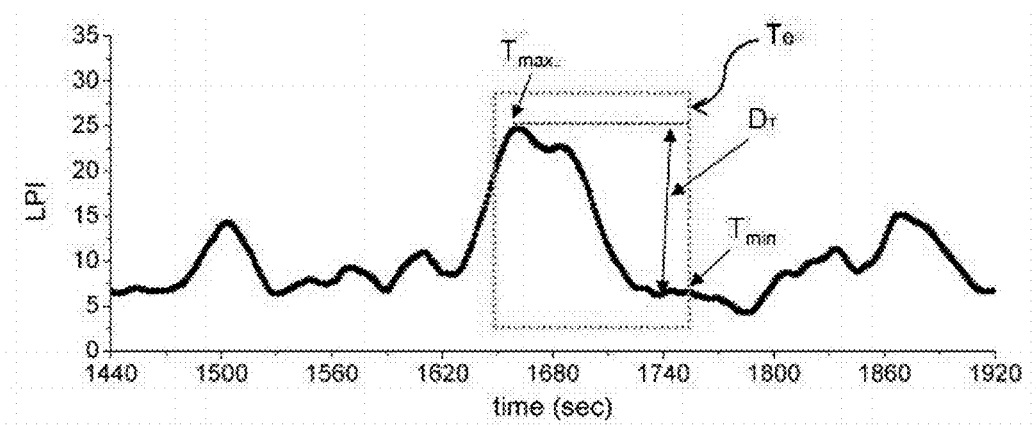
FIG. 11 is a graphic diagram showing the average value of the temperature differences, calculated in FIG. 10, as a function of time.

Herein, the processor 190 may also display the average difference value, calculated in the set unit time (N), on the display unit 150 as a function of time as shown in FIG. 11.

Then, the processor 190 determines whether a set elementary time (Te) has elapsed (S129), and if the elementary time (Te) has not elapsed, the processor 190 repeatedly performs the above steps (S122 to 5128) to repeatedly collect the average value of the temperature differences.

The average difference values are collected for the elementary time (Te), and if the elementary time (Te) has elapsed, whether cracking has occurred in the solidified shell 81 is diagnosed by calculating the maximum difference ($D_T$) using the maximum value ($T_{max}$) and minimum value ($T_{min}$) of the collected average values and comparing the calculated maximum difference value ($D_T$) with the preset reference value (S130). Herein, if the maximum value of the temperature differences is greater than the reference value, the processor 190 diagnoses that cracking has occurred in the solidified shell 81.

In FIG. 11, the y-axis is a longitudinal probability index (LPI) which is the average difference value calculated per unit time (N) for any line, and the x-axis is the time axis.

In general, the length of the continuously cast steel 80 that is drawn from the mold 30 may be about 0.9-2.3 m per min, and based on this length, the elementary time (Te) may be set in the range from 15 sec to 150 sec. If the elementary time (Te) is shorter than 15 sec, large cracks cannot be detected, and if the elementary time (Te) is longer than 150 sec, a temperature difference having no connection with cracks can be detected, resulting in a decrease in accuracy.

Herein, the unit time (N, or number) and the elementary time (Te) are information of different references, and the elementary time (Te) is set at a greater value than the unit time (N).

As described above, in the present invention, longitudinal cracks are diagnosed based on the variation in temperature of a solidified shell that is produced in a continuous casting process, so that only the surface of a slab in which longitudinal cracks have occurred can be scarfed, thus reducing the cost for correcting slabs. In particular, in the present invention, cracks occurring at positions corresponding to the temperature sensors of the second group can be more accurately detected.

Figure 12:
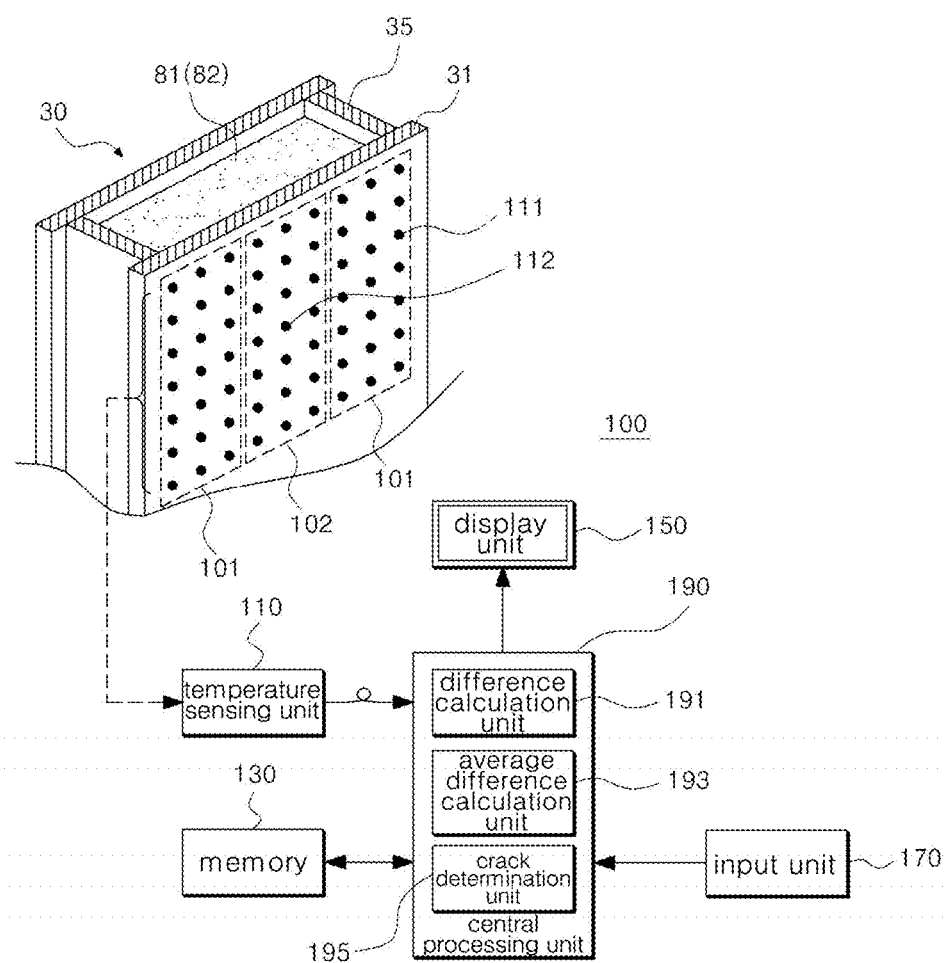
FIG. 12 shows a system for diagnosing cracking in a solidified shell in a mold according to a second embodiment of the present invention.

FIG. 12 shows a system for diagnosing cracks in a solidified shell in a mold according to a second embodiment of the present invention. As shown in FIG. 12, a crack diagnosis system 100 comprises a temperature sensing unit 110, a memory 130, a display unit 150, an input unit 170 and a processor 190.

The temperature sensing unit 110 comprises a plurality of temperature sensors 111 and 112 arranged in a matrix form on a long side 31 of the mold. The plurality of temperature sensors 111 and 112 arranged in the mold 30 sense in real-time the temperature of the mold 30 during a continuous casting process. The temperature of the mold 30 is regarded to be the same as that of a solidified shell 81 present in the mold 30.

Herein, the temperature sensors 111 and 112 have identification information for identifying the respective regions arranged in the mold 30. Thus, when the temperature of the mold 30 is sensed by each of the temperature sensors 111 and 112, the temperature sensing unit 110 transmits the sensed temperature information to the processor 190.

Figure 13:
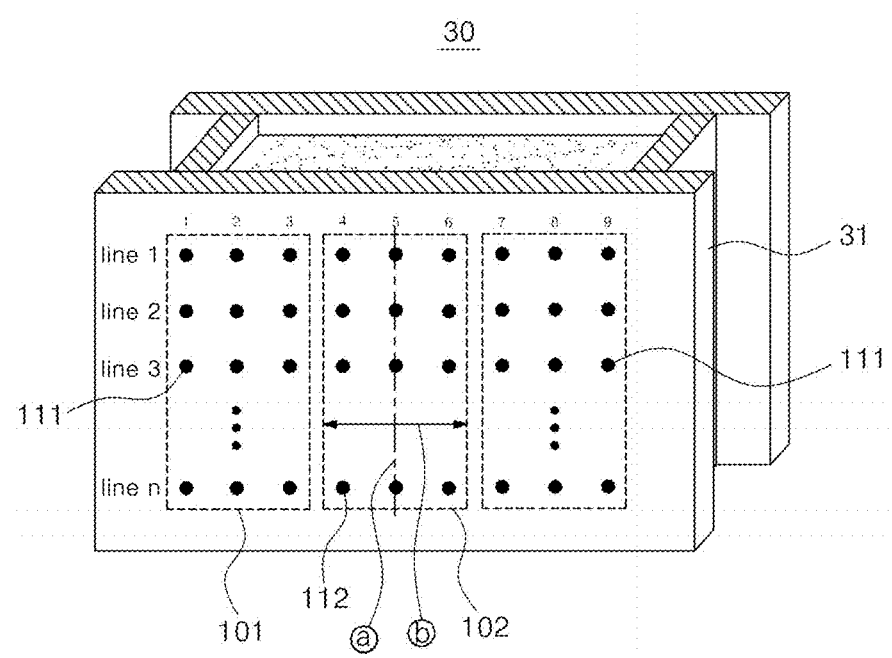
FIG. 13 shows temperature sensors arranged in the long side of a mold according to the present invention.

As shown in FIG. 13, the temperature sensors 111 and 112 of the temperature sensing unit 110 are arranged and embedded in the long side 31 of the mold in a matrix form. The temperature sensors 111 and 112 may be either of thermocouples and temperature sensors.

The plurality of temperature sensors 111 and 112 arranged in the mold 30 are divided into a first group 101 and a second group 102 with respect to a region in which cracks can occur. Generally, cracks occur in the central portion of the long side 31 of the mold. As shown in FIG. 13, the temperature sensors 112 belonging to the second group 102 are arranged in the central portion of the mold 30, and the temperature sensors 111 belonging to the first group 101 are disposed at both ends of the mold 30. The first group 101 includes at least one temperature sensors 111 disposed in the region in which no cracks occur, and the second group 102 includes at least one temperature sensors 112 disposed in the region in which cracks occur. Although the embodiment of the present invention illustrates that the first group 101 includes six temperature sensors 111 per line and the second group 102 includes three temperature sensors 112 per line, the number of the temperature sensors 111 and 112 may be changed as required.

Herein, the temperature sensors 112 belonging to the second group 102 are located at each of both sides of the central vertical line (a) of the mold 30, which is an area corresponding to 30% or less of the width of the mold 30. In other words, the second group 102 is located in the central portion of the long side 31 of the mold, which is a region (b) corresponding to about 30% of the width of the long side 31.

Although FIG. 13 illustrates that the plurality of temperature sensors 111 and 112 are arranged throughout the long side 31 of the mold, they may also be selectively arranged at the upper, lower or central portion of the long side 31 of the mold. It should be noted that, when the temperature sensors 111 and 112 are arranged throughout the long side 31 of the mold, accuracy for crack detection can be improved.

The memory 130 stores a time period and unit time for detection of the temperature of the mold 30, a reference value for determination of occurrence of cracks, various control programs, etc. The display unit 150 may display the difference in temperature between the first group 101 and the second group 102 or the average value of the temperature differences as a function of time. The display unit 150 may graphically display the change in the temperature difference.

The input unit 170 is configured such that it receives various operating commands or set values from the outside and transmits the received values to the processor 190.

The processor 190 acquires the average temperature value of the temperature sensors 111 of the first group 101 and the average temperature value of temperature sensors other than any one of the temperature sensors 112 of the second group 102 for each line from the temperatures detected by the temperature sensing unit 110, and uses the temperature difference between the acquired average temperature value of the first group 101 and the acquired average temperature value of the second group 102 to diagnose whether cracking has occurred in the solidified shell 81 that is discharged from the mold 30. Herein, the average temperature value of the first group 101 and the average temperature value of the second group are calculated for each line.

For example, as shown in FIG. 13, when the temperature sensors 111 and 112 are arranged in a matrix of N (lines)×9 (rows), the first group 101 consists of the temperature sensors 111 belonging to rows 1, 2, 3, 7, 8 and 9, and the second group 102 consists of the temperature sensors 112 belonging to rows 4, 5 and 6.

The processor 190 calculates the average temperature value for each line using the temperature information detected by the temperature sensors 111 disposed in rows 1, 2, 3, 7, 8 and 9, and calculates the average temperature value of temperature sensors other than any one of the temperature sensors 112 disposed in rows 4, 5 and 6. Herein, the other temperature sensors of the second group 102 are preferably temperature sensors adjacent to each other. For example, when the temperature sensors 112 of the second group 102 are those located in rows 4, 5 and 6, the processor calculates the average temperature value of the temperature sensors located in rows 4 and 5 or calculates the average temperature value of the temperature sensors located in rows 5 and 6.

Then, the processor 190 calculates the temperature difference by subtracting the average temperature value of the second group 102 from the average temperature value of the first group 101 and temporarily stores the calculated temperature difference in the memory 130.

Herein, the processor 190 may repeatedly acquire the average temperature value of the first group 101, the average temperature value of the second group 102 and the temperature difference therebetween one or more times. The average value of the repeatedly acquired temperature differences is compared with a preset reference value, and based on the comparison result, whether cracking has occurred in the solidified shell 81 is diagnosed for each line.

Figure 14:
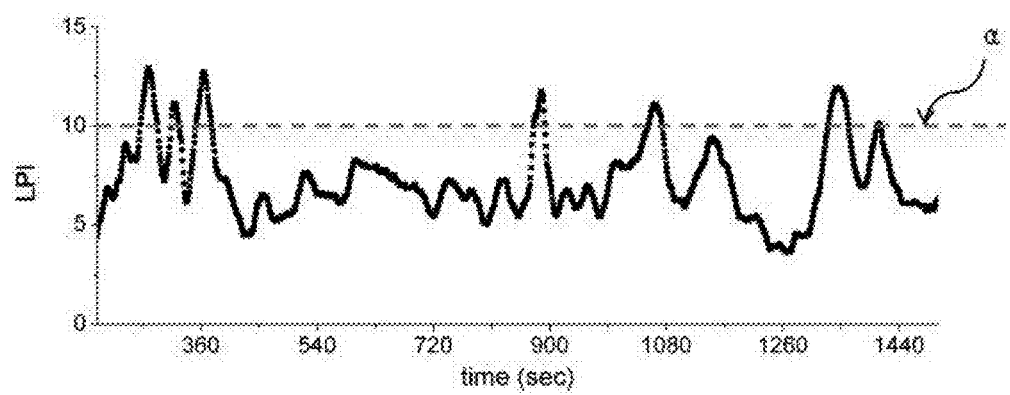
FIG. 14 is a graphic diagram showing the average value of the temperature differences, calculated in FIG. 12, as a function of time.

As shown in FIG. 14, the processor 190 may also display an average difference value (LPI) for any line, calculated per set unit time, on the display unit 150 as a functional of time.

In FIG. 14, the y-axis is a longitudinal probability index (LPI) which is an average difference value calculated per unit time (N) for any line, and the x-axis is the time axis. As shown in FIG. 14, in the embodiment of the present invention, the reference value ($\alpha$) is set at 10, and if the average difference value (LPI) is greater than 10, the processor 190 determines that longitudinal cracks have occurred in the solidified shell 81 in the mold 30. Herein, the reference value ($\alpha$) may differ between the lines in which the temperature sensors 111 and 112 are disposed.

Figure 15:
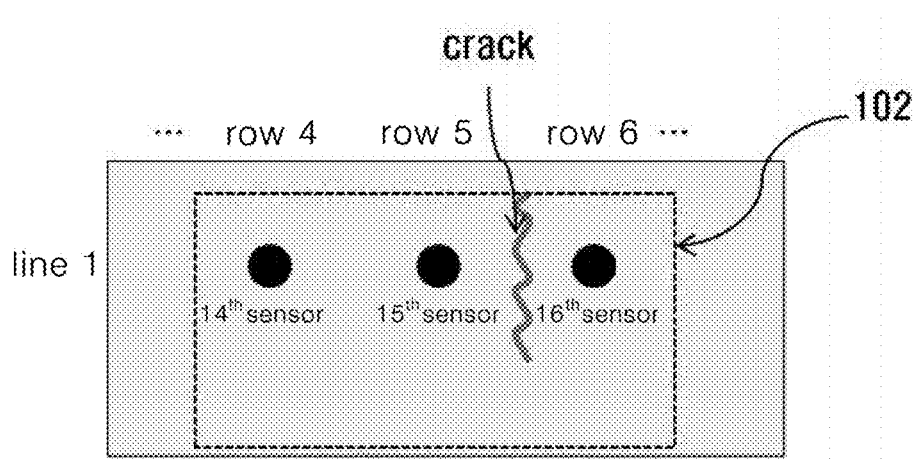
FIG. 15 shows cracking in a mold.

In other words, as shown in FIG. 15, if the average difference value (LPI) is greater than the reference value ($\alpha$), it is determined that longitudinal cracks have occurred at the central portion of the long side 31 of the mold, that is, the portion of the solidified shell 81 that corresponds to the second group 102. If cracks occur at the portion of the solidified shell 81 that corresponds to a portion between rows 5 and 6 of line 1, the temperatures of the mold 30 detected by a $15^{th}$ sensor and a $16^{th}$ sensor will be lower than the temperatures of the mold 30 detected by a $14^{th}$ sensor located at row 4. The crack diagnosis algorithm according to the present invention shows relatively excellent crack diagnosis performance when cracking occurs at portions between the temperature sensing sensors of the second group 102 as shown in FIG. 15.

The processor 190 may comprise a difference calculation unit 191, an average-difference calculation unit 193 and a crack determination unit 195.

The difference calculation unit 191 acquires each of the average temperature value of the temperature sensors 111 of the first group 101 and the average temperature value of temperature sensors other than any one of the temperature sensors 112 of the second group 102 for each line, and calculates the temperature difference between the acquired average temperature value of the first group 101 and the acquired temperature value of the second group 102. Of course, the difference calculation unit 191 may periodically acquire the average temperature value of the first group 101 and the average temperature value of the second group 102, calculate the temperature difference between the acquired temperature values and temporarily store the calculated temperature difference together with the measurement time information in the memory 130.

The average-difference calculation unit 193 reads the temperature differences, repeatedly acquired for the set time, from the memory 130, and calculates the average value of the temperature differences per set unit time.

The crack determination unit 195 diagnoses whether cracking has occurred in the solidified shell 81 for each line by comparing a preset reference value with the average value of the temperature differences calculated by the average-difference calculation unit 193.

The processor 190 may also display the average value of the temperature differences, calculated by the average-difference calculation unit 193, on the display 150.

Meanwhile, the processor 190 acquires each of the average temperature value of the temperature sensors 111 of the first group and the average temperature value of temperature sensors other than any one of the temperature sensors 112 of the second group 102 from the temperatures detected by the temperature sensing unit 110 for each line, and stores the temperature difference between the acquired average temperatures of the first and second groups together with the measurement time information. Herein, the processor 190 may repeatedly acquire the average temperature value of the first group 101, the average temperature value of the second group 102 and the temperature difference therebetween one or more times, and collects the average value of the repeatedly acquired temperature differences for a set elementary time. Whether cracking has occurred in the solidified shell 81 may be diagnosed for each line by collecting the average difference values for an elementary time and comparing the maximum value of the collected average difference values with a preset reference value.

In addition, the processor 190 may also diagnose whether cracking has occurred in the solidified shell, by repeatedly acquiring the average temperature value of the first group 101, the average temperature value of the second group 102 and the temperature difference therebetween one or more times for each line, and comparing the maximum value of the average values of the repeatedly acquired temperature differences for each line with a preset reference value.

Figure 16:
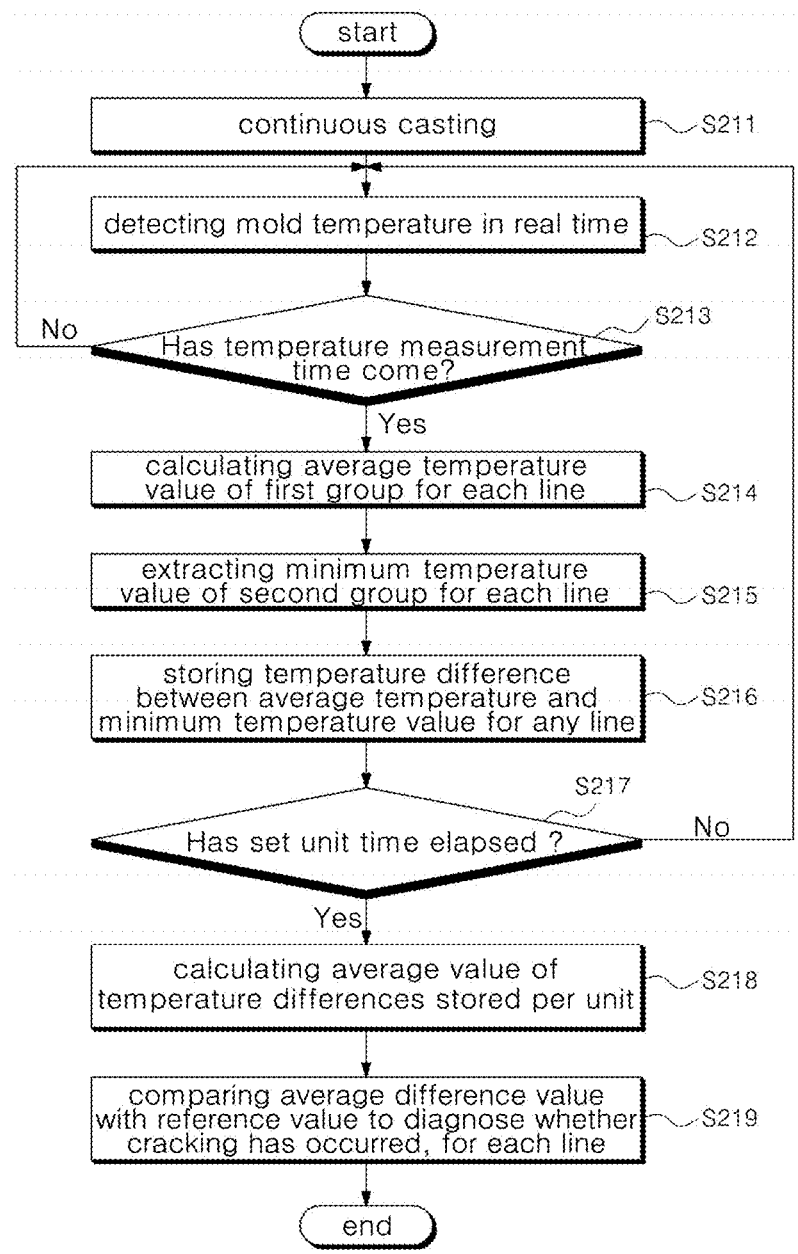
FIG. 16 is a flowchart showing a process for diagnosing cracking in a solidified shell according to one embodiment of FIG. 12.

FIG. 16 is a flowchart showing the process for diagnosing cracking in a solidified shell according to the embodiment of FIG. 12.

Referring to FIG. 16, during a continuous casting process, the temperature sensing unit 110 senses in real-time the temperatures of regions of the mold 30 in which the temperature sensors 111 and 112 are disposed, and transmits the sensed temperatures to the processor 190 (S211 and S212). Herein, the temperature sensing unit 110 transmits the identification information of each of the temperature sensors 111 and 112 together with temperature information to the processor 190, and from the transmitted identification information, the processor 190 determines whether the temperature information belongs to the first group 101 or the second group 102.

The plurality of temperature sensors 111 and 112 are divided into the first group 101 and the second group 102 with respect to a region in which cracking can occur. The first group 101 is disposed in both edges of the long side 31 of the mold, in which no cracking occurs, and the second group 102 is disposed in the central portion of the long side 31 of the mold, in which cracking occurs.

When the set temperature measurement time (T) is reached, the processor 190 calculates the average temperature value of the temperature sensors 111 of the first group 101 for any line using the temperature information of the temperature sensors 111 of the first group 101 present in the region in which no cracking occurs (S214).

After calculating the average temperature value for the first group 101, the processor 190 calculates the average temperature value of temperature sensors other than any one of the temperature sensors 112 of the second group 102 in any line, which is present in the region in which cracking occurs (S215).

The processor 190 calculates the temperature difference by subtracting the acquired average temperature value of the second group 102 from the acquired average temperature value of the first group 101, and temporarily stores the calculated temperature difference together with the measurement time information in the memory 130 (S216). Herein, the processor 190 may display the calculated temperature difference as a function of time on the display unit 150.

Then, the processor 190 determines whether the set unit time (N, or the number of unit times) has elapsed (S217), and if the set unit time has not elapsed, the above steps (S214 to 5216) are repeated to acquire the average temperature value of the first group 101, the average temperature value of the second group 102 and the temperature difference therebetween again, and the acquired temperature difference together with the measurement time information is temporarily stored in the memory 130.

This process is repeatedly performed for the set unit time (N).

If the set unit time (N, or unit time) has elapsed (S217), the processor 190 reads the repeatedly acquired temperature differences from the memory 130 and calculates the average value of the temperature differences (S218), and it diagnoses whether cracking has occurred in the solidified shell 81 for each line by comparing the calculated average difference value to the preset reference value ($\alpha$) (S219). Herein, if the average value of the temperature differences is greater than the reference value ($\alpha$), the processor 190 diagnoses that cracking has occurred in the solidified shell 81.

The processor 190 may display the average difference value for any line, calculated per set unit time (N), on the display unit 150 as a function of time as shown in FIG. 14.

Meanwhile, whether cracking has occurred in the solidified shell may also be diagnosed by comparing the maximum value of the average values of the temperature differences for each line, repeatedly acquired in the above steps (S212 to S218), with the preset reference value.

Figure 17:
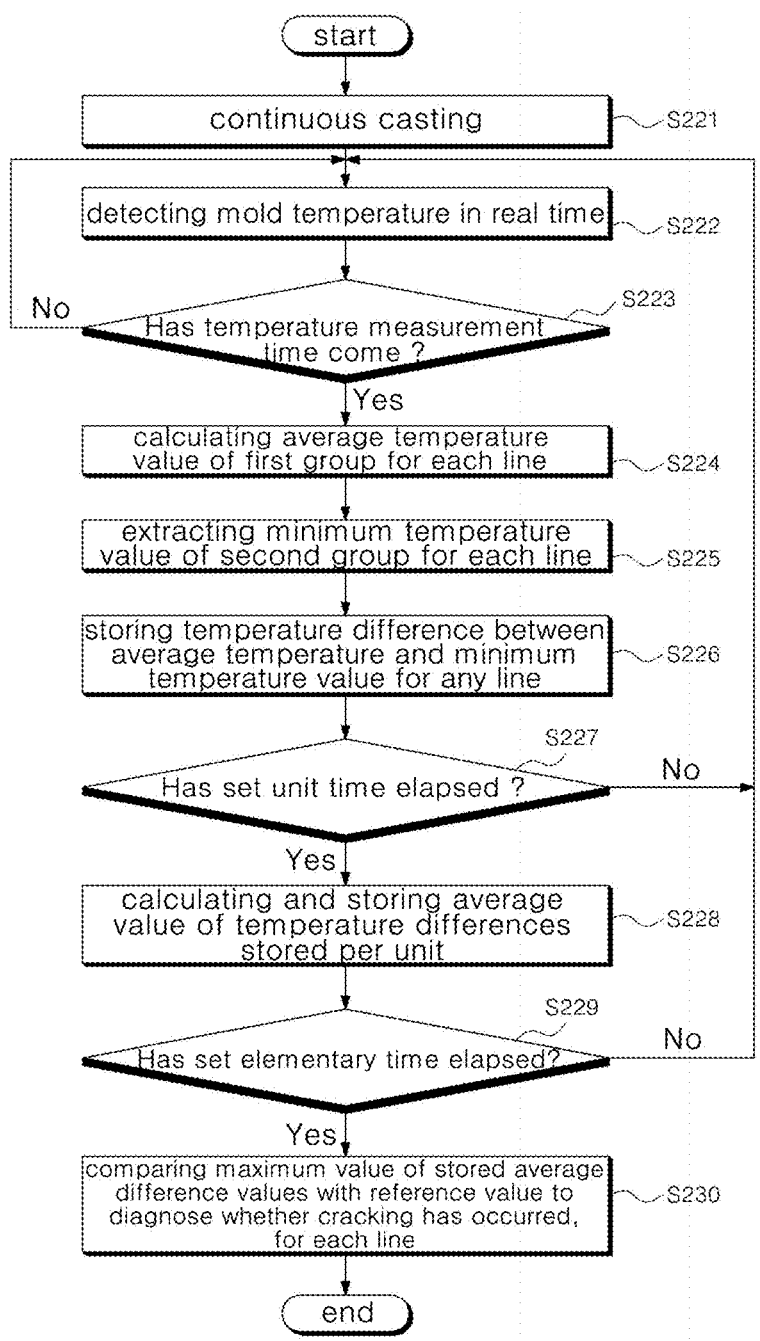
FIG. 17 is a flowchart showing a process for diagnosing cracking in a solidified shell according to one embodiment of FIG. 12.

FIG. 17 is a flowchart showing a process for diagnosing cracking in a solidified shell according to another embodiment of FIG. 12.

Referring to FIG. 17, during a continuous casting process, the temperature sensing unit 110 senses in real-time the temperatures of regions of the mold 30 in which the temperature sensors 111 and 112 are disposed, and transmits the sensed temperatures to the processor 190 (S221 and S222).

The plurality of temperature sensors 111 and 112 are divided into the first group 101 and the second group 102 with respect to a region in which cracking can occur. The first group 101 is disposed at both sides of the long side 31 of the mold in which no cracking occurs, and the second group 102 is disposed in the central portion of the long side 31 of the mold in which cracking occurs.

When the set temperature measurement time (T) is reached (S223), the processor 190 calculates the average temperature value of the temperature sensors 111 of the first group 101 for each line using the temperature information of the temperature sensors 111 of the first group 101 present in the region in which no cracking occurs (S224).

After calculating the average temperature value of the first group 101, the processor 190 calculates the average temperature value of temperature sensors other than any one of the temperature sensors 112 of the second group 102 for each line, which is present in the region in which cracking occurs (S225).

The processor 190 calculates the temperature difference by subtracting the acquired average temperature value of the second group 102 from the acquired average temperature value of the first group 101 for each line, and temporarily stores the calculated temperature difference together with the measurement time information in the memory 130 (S226). Herein, the processor 190 may display the calculated temperature difference as a function of time on the display unit 150.

Then, the processor 190 determines whether the set unit time (N, or the number of unit times) has elapsed (S227), and if the set unit time has not elapsed, the above steps (S222 to 5226) are repeated to acquire the average temperature value of the first group 101, the average temperature value of the second group 102 and the temperature difference therebetween again, and the acquired temperature difference together with the measurement time information is temporarily stored in the memory 130.

This process is repeatedly performed for the set unit time (N).

If the set unit time (N, or the number of unit times) has elapsed (S227), the processor 190 reads the repeatedly acquired temperature differences from the memory 130, calculates the average value of the temperature differences and temporarily stores the calculated average value in the memory 130 (S228).

Figure 18:
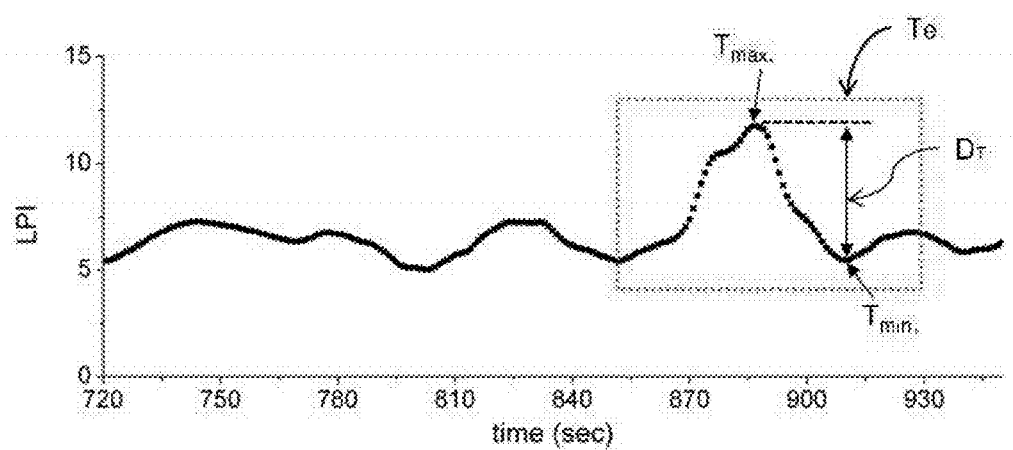
FIG. 18 is a graphic diagram showing the average value of the temperature differences, calculated in FIG. 17, as a function of time.

The processor 190 may display the average difference value, calculated per set unit time (N), on the display unit 150 as a function of time as shown in FIG. 18.

Then, the processor 190 determines whether the set elementary time (Te) has elapsed (S229), and if the elementary time (Te) has not elapsed, the above steps (S222 to S228) are repeatedly performed to repeatedly collect the average value of the temperature differences.

The average difference values are collected for the elementary time (Te), and if the elementary time (Te) has elapsed, whether cracking has occurred in the solidified shell 81 is diagnosed by calculating the maximum difference ($D_T$) using the maximum value ($T_{max}$) and minimum value ($T_{min}$) of the collected average difference values and comparing the calculated maximum difference ($D_T$) with the preset reference value (S230). If the maximum value of the temperature differences is greater than the reference value, the processor 190 diagnoses that cracking has occurred in the solidified shell 81.

In FIG. 18, the y-axis is a longitudinal probability index (LPI) which is the average difference value calculated per unit time (N) for any line, and the x-axis is the time axis.

In general, the length of the continuously cast steel 80 that is drawn from the mold 30 may be about 0.9-2.3 m per min, and based on this length, the elementary time (Te) may be set in the range from 15 sec to 150 sec. If the elementary time (Te) is shorter than 15 sec, large cracks cannot be detected, and if the elementary time (Te) is longer than 150 sec, a temperature difference having no connection with cracks can be detected, resulting in a decrease in accuracy.

Herein, the unit time (N, or the number of times) and the elementary time (Te) are information of different references, and the elementary time (Te) is set at a greater value than the unit time (N).

As described above, in the present invention, longitudinal cracks are diagnosed based on the variation in temperature of a solidified shell that is produced in a continuous casting process, so that only the surface of a slab in which longitudinal cracks have occurred can be scarfed, thus reducing the cost for correcting slabs. In particular, in the present invention, cracks occurring at the positions between the temperature sensors of the second group can be more accurately detected.

Figure 19:
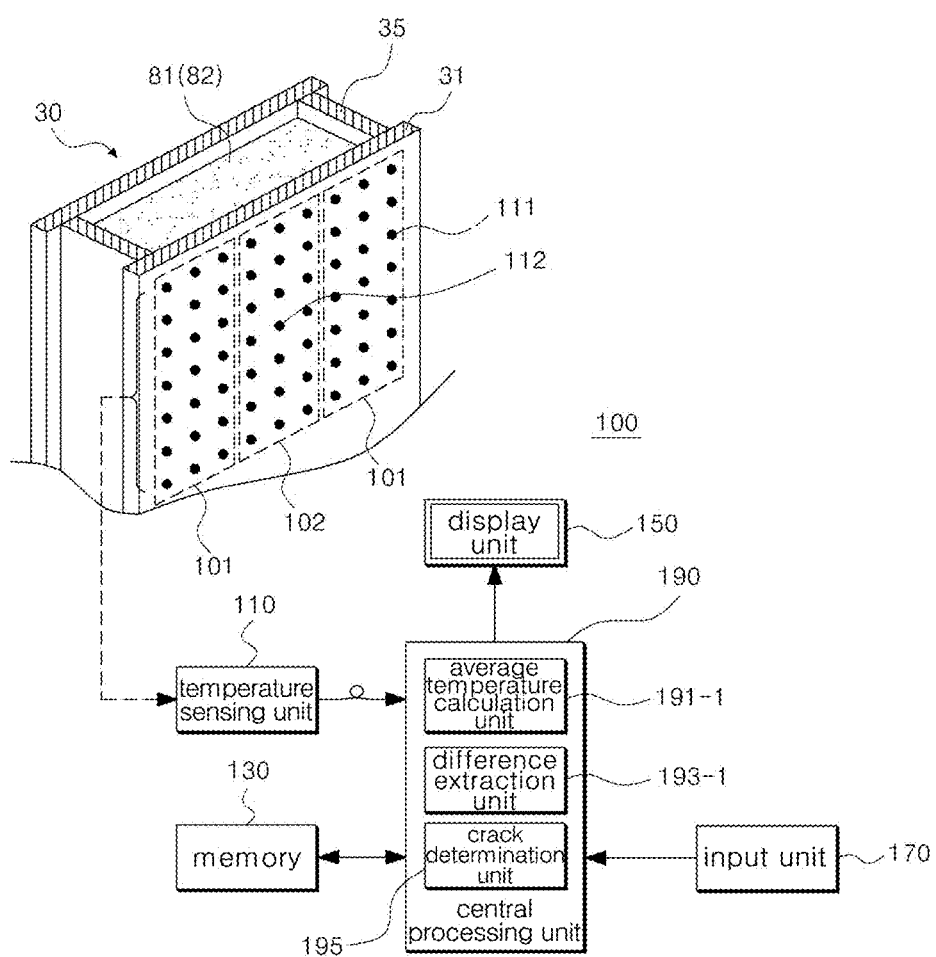
FIG. 19 shows a system for diagnosing cracking in a solidified shell in a mold according to a third embodiment of the present invention.

FIG. 19 shows a system for diagnosing cracking in a solidified shell in a mold according to a third embodiment of the present invention. As shown therein, a crack diagnosis system 100 comprises a temperature sensing unit 110, a memory 130, a display unit 150, an input unit 170 and a processor 190.

The temperature sensing unit 110 comprises a plurality of temperature sensors 111 and 112 arranged in a matrix form in the long side 31 of the mold. The plurality of temperature sensors 111 and 112 arranged in the mold 30 sense in real-time the temperature of the mold 30 during a continuous casting process. The temperature of the mold 30 is regarded to be the same as that of the solidified shell present in the mold 30.

Herein, the temperature sensors 111 and 112 have identification information for identifying the respective regions arranged in the mold 30. Thus, when the temperature of the mold 30 is sensed by each of the temperature sensors 111 and 112, the temperature sensing unit 110 transmits the sensed temperature information to the processor 190.

Figure 20:
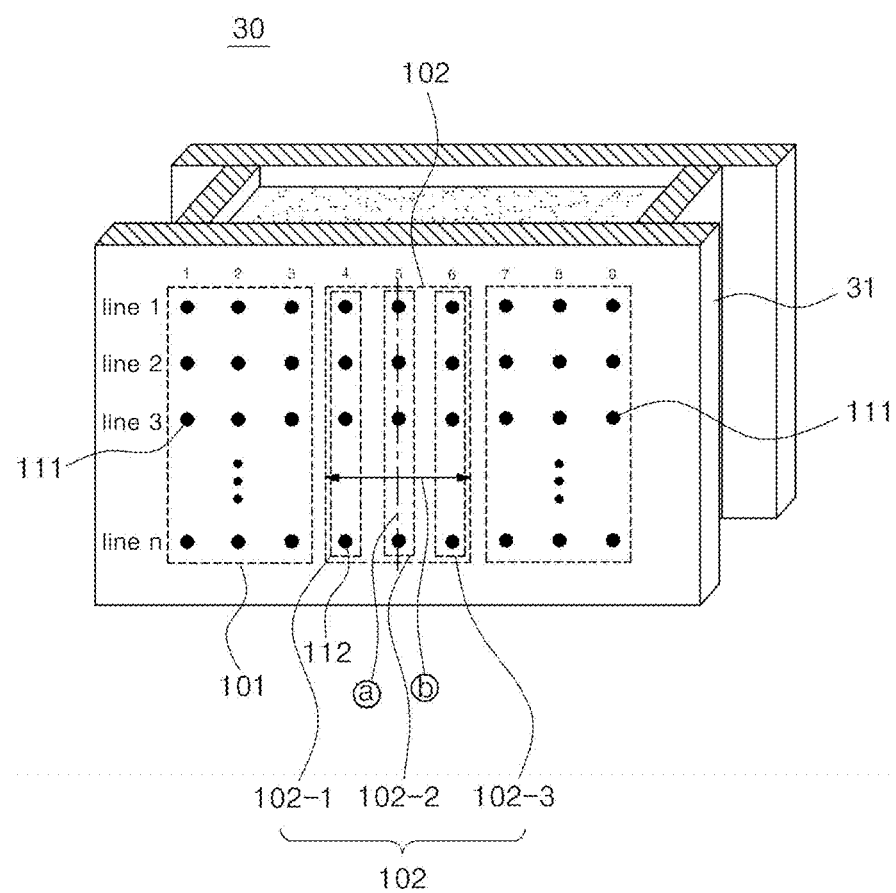
FIG. 20 shows temperature sensors arranged in the long side of a mold according to the present invention.

As shown in FIG. 20, the temperature sensors 111 and 112 of the temperature sensing unit 110 are arranged and embedded in the long side 31 of the mold in a matrix form. The temperature sensors 111 and 112 may be either of thermocouples and temperature sensors.

The plurality of temperature sensors 111 and 112 arranged in the mold 30 are divided into a first group 101 and a second group 102 with respect to a region in which cracking can occur. As shown in FIG. 20, the temperature sensors 112 belonging to the second group 102 are disposed in the central portion of the mold 30, and the temperature sensors 111 belonging to the first group 101 are disposed in both edges of the mold 30. The first group 101 includes at least one temperature sensors 111 disposed in the region in which no cracking occurs, and the second group 102 includes at least one temperature sensors 112 disposed in the region in which cracking occurs. Although the embodiment of the present invention illustrates that the first group includes six temperature sensors 111 per line and the second group 102 includes three temperature sensors per line, the number of the temperature sensors 111 and 112 can be changed as required.

Herein, the temperature sensors 112 belonging to the second group 102 are located at each of both sides of the central vertical line ⓐ of the mold 30, which is an area corresponding to 30% or less of the width of the mold 30. In other words, the second group 102 is located in the central portion of the long side 31 of the mold, which is a region ⓑ corresponding to about 30% of the width of the long side 31.

Although FIG. 20 illustrates that the plurality of temperature sensors 111 and 112 are arranged throughout the long side 31 of the mold, they may also be selectively arranged at the upper, lower or central portion of the long side 31 of the mold. It should be noted that, when the temperature sensors 111 and 112 are arranged throughout the long side 31 of the mold, accuracy for crack detection can be improved.

The memory 130 stores a time period of the temperature of the mold 30, a reference value for determination of occurrence of cracks, various control programs, etc.

The display unit 150 may display the temperature difference between the first group 101 and the second group 102 as a function of time. Also, the display unit 150 may graphically display the change in the temperature difference.

The input unit is configured such that it receives various operating commands or set values from the outside and transmits these values to the processor 190.

The processor 190 calculates each of the average temperature of the first group 101 and the average temperature of each row of the second group from the temperatures detected by the temperature sensing unit 110, extracts the maximum temperature difference by subtracting the calculated average temperature of each row of the second group from the calculated average temperature of the first group, and comparing the extracted maximum temperature difference with a preset reference value, thereby diagnosing whether cracking has occurred in the solidified shell 81 that is discharged from the mold 30. Herein, the average temperature of the first group is the average temperature of the temperatures detected by all the temperature sensors of the first group, and the average temperature of each row of the second group is the average temperature of the temperatures detected by the temperature sensors of each row of the second group.

For example, when the temperature sensors 111 and 112 are arranged in a matrix of N (lines)×9 (rows) as shown in FIG. 20, the first group 101 consists of the temperature sensors 111 belonging to rows 1, 2, 3, 7, 8 and 9, and the second group 102 consists of the temperature sensors 112 belonging to rows 4, 5 and 6. Thus, the average temperature of the first group 101 is the average temperature of all the temperature sensors belonging to rows 1, 2, 3, 7, 8 and 9, and the average temperature of each row of the second group 102 can be divided into an average temperature for row 4 (102-1), an average temperature for row 5 (102-2), and an average temperature for row 6 (102-3).

The processor 190 may comprise an average-temperature calculation unit 191-1, a difference extraction unit 193-1 and a crack determination unit 195.

The average-temperature calculation unit 191-1 calculates each of the average temperature of the temperature sensors 111 of the first group 101 and the average temperature of the temperature sensors 112 in each of rows 102-1 to 102-3 of the second group 102 from the temperatures detected by the temperature sensing unit 110.

The difference extraction unit 193-1 extracts the maximum temperature difference by subtracting the average temperature of each of rows 102-1 to 102-3 of the second group 102 from the calculated average temperature of the first group 101. Of course, the difference extraction unit 191 may temporarily store the extracted average temperature of the first group 101, the average temperature of each of rows 102-1 to 102-3 of the second group 102, and the maximum temperature difference, together with the measurement time information, in the memory 130.

The crack determination unit 195 diagnoses whether cracking has occurred in the solidified shell, by comparing the maximum temperature difference, extracted by the difference extraction unit 193-1, with a preset reference value.

The processor 190 may display the maximum temperature difference, calculated by the difference extraction unit 190, on the display unit 150.

Meanwhile, the processor 190 calculates each of the average temperature of the first group 101 and the average temperature of each of rows 102-1 to 102-3 of the second group 102 from the temperatures detected by the temperature sensing unit 110, extracts each of the maximum temperature difference and the minimum temperature difference by subtracting the calculated average temperature of each of rows 102-1 to 102-3 of the second group 102 from the calculated average temperature of the first group 101, and uses the extracted maximum temperature difference and minimum temperature difference to diagnose whether cracking has occurred in the solidified shell. When whether cracking has occurred in the solidified shell is diagnosed, the processor 190 acquires the temperature difference by subtracting the extracted minimum temperature difference from the maximum temperature difference, compares the acquired temperature difference with a preset reference value, and diagnoses that cracking has occurred in the solidified shell 81, if the acquired temperature difference is greater than the reference value. Herein, the average temperature of the first group 101 is the average temperature of the temperatures detected by all the temperature sensors 111 of the first group 101, and the average temperature of each of rows 102-1 to 102-3 of the second group 102 is the average temperature of the temperatures detected by the temperature sensors 112 of each of rows 102-1 to 102-3 of the second group 102.

The processor 190 may comprise an average-temperature calculation unit 191-1, a difference extraction unit 193-1 and a crack determination unit 195.

The average-temperature calculation unit 191-1 calculates each of the average temperature of the temperature sensors 111 of the first group 101 and the average temperature of the temperature sensors 112 of each of rows 102-1 to 102-3 of the second group 102 from the temperatures detected by the temperature sensing unit 110.

The differentiation extraction unit 193-1 extracts each of the maximum temperature difference and the minimum temperature difference by subtracting the calculated average temperature of each of rows 102-1 to 102-3 of the second group 102 from the average temperature of the first group 101. Of course, the difference extraction unit 193-1 can temporarily store the extracted average temperature of the first group, the average temperature of each of rows 102-1 to 102-3 of the second group 102, the maximum temperature difference and the minimum temperature difference, together with the measurement time information, in the memory 130.

The crack determination unit 195 diagnoses whether cracking has occurred in the solidified shell, by subtracting the minimum temperature difference from the maximum temperature difference extracted by the difference extraction unit 193-1 and comparing the temperature difference, obtained by the subtraction, with a preset reference value.

The processor 190 may display on the display unit 150 the temperature difference between the maximum temperature difference and the minimum temperature difference, calculated by the crack determination unit 193.

Figure 21:
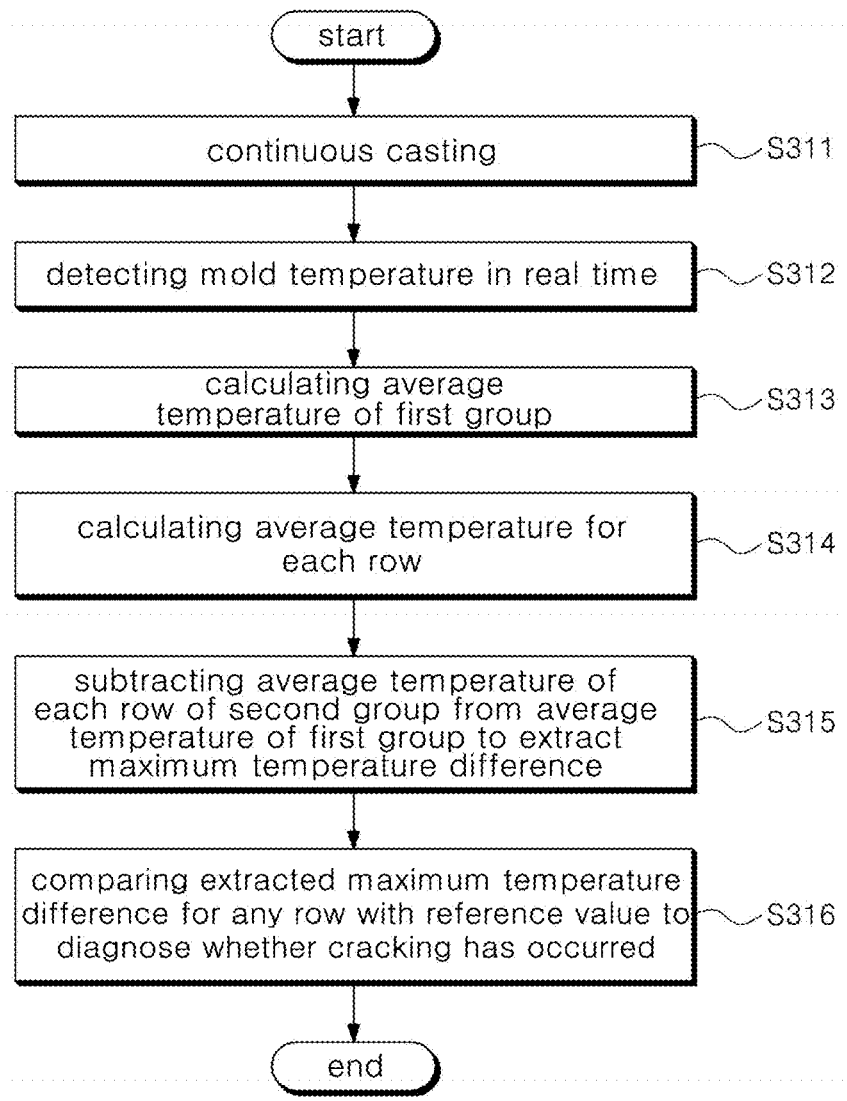
FIG. 21 is a flowchart showing a process for diagnosing cracking in a solidified shell according to one embodiment of FIG. 19.

FIG. 21 is a flowchart showing a process for diagnosing cracking in a solidified shell according to an embodiment of FIG. 19.

Referring to FIG. 21, during a continuous casting process, the temperature sensing unit 110 senses in real-time the temperature of regions of the mold 30 in which the temperature sensors 111 and 112 are disposed, and transmits the sensed temperature to the processor 190 (S311 and S312). Herein, the temperature sensing unit 110 transmits the identification information of each of the temperature sensors 111 and 112 together with the temperature information to the processor 190, and from the transmitted identification information, the processor 190 determines whether the temperature information belongs to the first group 101 or the second group 102.

The plurality of temperature sensors 111 and 112 are divided into a first group 101 and a second group 102 with respect to a region in which cracking can occur. The first group is disposed in both edges of the long side 31 of the mold, in which no cracking occurs, and the second group 102 is disposed in the central portion of the long side 31 of the mold, in which cracking occurs.

When the set temperature measurement time comes, the processor 190 calculates the average temperature of the first group 101 using the temperature information of the temperature sensors 111 of the first group 101 present in the region in which no cracking occurs (S313).

After calculating the average temperature of the first group 101, the processor 190 calculates the average temperature of the temperatures detected by the temperature sensors 112 of each of rows 102-1 to 102-3 of the second group 102 present in the region in which cracking occurs (S314). In other words, in the first group 101, there is one average temperature value regardless of the number of rows, but in the second group 102, there are three average temperature values if the number of rows is 3.

The processor 190 extracts the maximum temperature difference by subtracting the calculated average temperature of each of rows 102-1 to 102-3 of the second group 102 from the average temperature of the first group (S315), and temporarily stores the extracted maximum temperature difference together with the measurement time information in the memory 130. Herein, the processor 190 may display the calculated maximum temperature difference as a function of time on the display unit 150. If the temperature sensors of the second group 102 consist of three rows, three temperature difference values will be produced by subtracting the average temperature of each of rows 102-1 to 102-3 of the second group 102 from the average temperature of the first group 101, and the processor will extract the maximum temperature difference value among the three temperature difference values.

Then, the processor 190 diagnoses whether cracking has occurred in the solidified shell, by comparing the extracted maximum temperature difference with a preset reference value (S316). If the maximum temperature difference is greater than the reference value, the processor 190 determines that cracking has occurred in the solidified shell 81.

Figure 22:
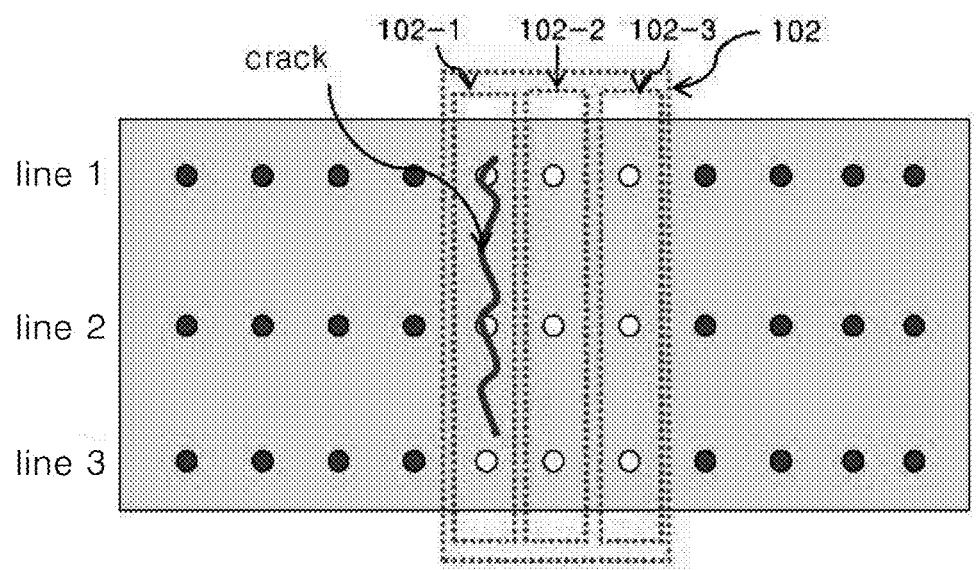
FIG. 22 shows cracking in a mold.

If the extracted maximum temperature difference is greater than the reference value, as shown in FIG. 22, it is diagnosed that longitudinal cracking has occurred in the central portion of the long side 31 of the mold, that is, the portion of the solidified shell 81 that corresponds to the second group 102. Further, cracking in the solidified shell in the mold is attributable to heat resulting from the maximum temperature difference. For example, if the maximum temperature difference occurs in row 102-1 among rows 4 to 6 of the second group 102, as shown in FIG. 22, longitudinal cracking will occur in the solidified shell in the mold. The crack diagnosis algorithm according to the present invention shows relatively excellent performance for detecting large longitudinal cracks occurring along the longitudinal direction of the second group 102 as shown in FIG. 22.

Figure 23:
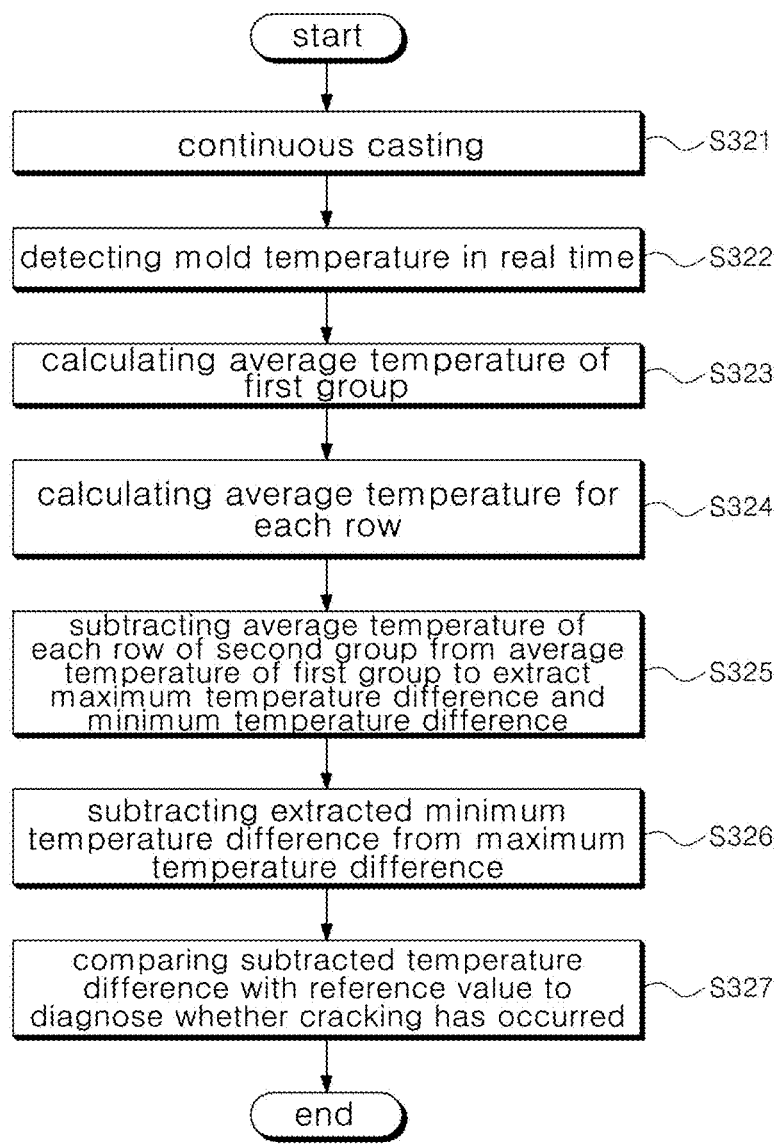
FIG. 23 is a flowchart showing a process for diagnosing cracking in a solidified shell according to another embodiment of FIG. 19.

FIG. 23 is a flowchart showing a process for diagnosing cracking in a solidified shell according to another embodiment of FIG. 19.

As shown in FIG. 23, during a continuous casting process, the temperature sensing unit 110 senses in real-time the temperatures of regions of the mold 30 in which the temperature sensors 111 and 112 are disposed, and transmits the sensed temperatures to the processor 190 (S321 and S322).

The plurality of temperature sensors 111 and 112 are divided into a first group 101 and a second group 102 with respect to a region in which cracking can occur. The first group 101 is disposed in both edges of the long side 31 of the mold in which no cracking occurs, and the second group 102 is disposed in the central portion of the long side 31 of the mold in which cracking occurs.

When the set temperature measurement time comes, the processor 190 calculates the average temperature of the first group 101 using the temperature information of the temperature sensors 111 of the first group 101 present in the region in which no cracking occurs (S323).

After calculating the average temperature of the first group 101, the processor calculates the average temperature of each of rows 102-1 to 102-3 from the temperatures detected by the temperature sensors 112 of the second group 102 present in the region in which cracking occurs (S324). In other words, in the first group 101, there is one average temperature value regardless of the number of rows, but in the second group 102, there are three average temperature values if the number of rows is 3.

The processor 190 extracts the maximum temperature difference and the minimum temperature difference by subtracting the calculated average temperature of each of rows 102-1 to 102-3 of the second group 102 from the average temperature of the first group 101 (S325). If the temperature sensors of the second group 102 consist of three rows, three temperature differences will be produced by subtracting the average temperature of each of rows 102-1 to 102-3 of the second group 102 from the average temperature of the first group 101, and the processor 190 will extract each of the maximum temperature difference and the minimum temperature difference among the three temperature difference values.

Then, the processor 190 subtracts the minimum temperature difference from the extracted maximum temperature difference (S326), and then compares the temperature difference, obtained by the subtraction, with a preset reference value, thereby diagnosing whether cracking has occurred in the solidified shell (S327). If the acquired temperature difference is greater than the reference value, the processor 190 diagnoses that cracking has occurred in the solidified shell 81. Herein, the processor may display the acquired temperature difference as a function of time on the display unit 150.

If it is diagnosed that cracking has occurred in the solidified shell in the mold, the occurrence of cracking will be attributable to the heat of the second group 102 in which the maximum temperature difference, not the minimum temperature difference, has occurred.

Figure 24:
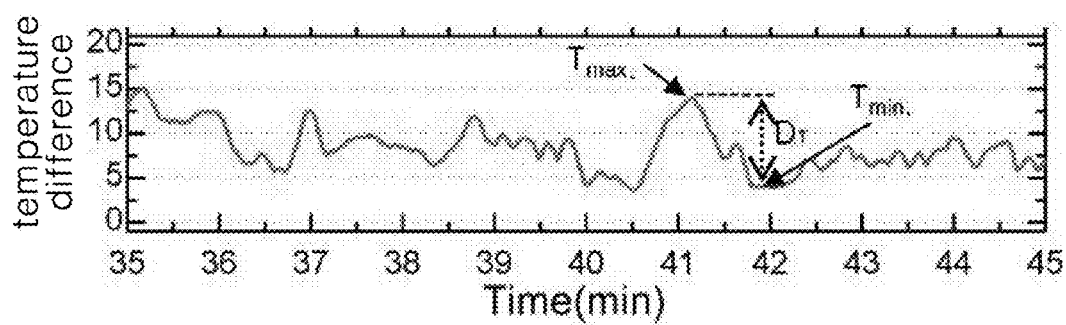
FIG. 24 is a graphic diagram showing the average value of the temperature differences, calculated in FIG. 23, as a function of time.

In FIG. 24, the y-axis shows the temperature difference, calculated by the process of FIG. 23, as a function of time, and the temperature difference of the y-axis is one obtained by subtracting the average temperature of each of rows 102-1 to 102-3 of the second group 102 from the average temperature of the first group 101.

As shown in FIG. 24, if the temperature difference ($D_T$) obtained by subtracting the minimum temperature difference (Tmin) from the maximum temperature difference (Tmax) is greater than the set reference value, it is diagnosed that cracking has occurred in the solidified shell 81 in the mold 30.

In other words, if the temperature difference is greater than the reference value, as shown in FIG. 22, it is diagnosed that longitudinal cracking has occurred in the portion of the solidified shell 81 that corresponds to the second group 102 present in the central portion of the long side 31 of the mold. For example, if the maximum temperature difference occurs in row 4 (102-1) among rows 4 to 6 of the second group 102 and the temperature difference obtained by subtracting the minimum temperature difference of any one row (row 5 or 6) from the maximum temperature difference is greater than the reference value, it is determined that longitudinal cracking has occurred in row 4 of the second group 102. The crack diagnosis algorithm according to the present invention shows relatively excellent performance for detection of large longitudinal cracks occurring along the longitudinal direction of the second group 102.

As described above, in the present invention, longitudinal cracks are diagnosed based on the variation in temperature of a solidified shell that is produced in a continuous casting process, so that only the surface of a slab in which longitudinal cracks have occurred can be scarfed, thus reducing the cost for correcting slabs. In particular, in the present invention, cracks occurring at positions corresponding to the temperature sensors of the second group 102 can be more accurately detected.

Figure 25:
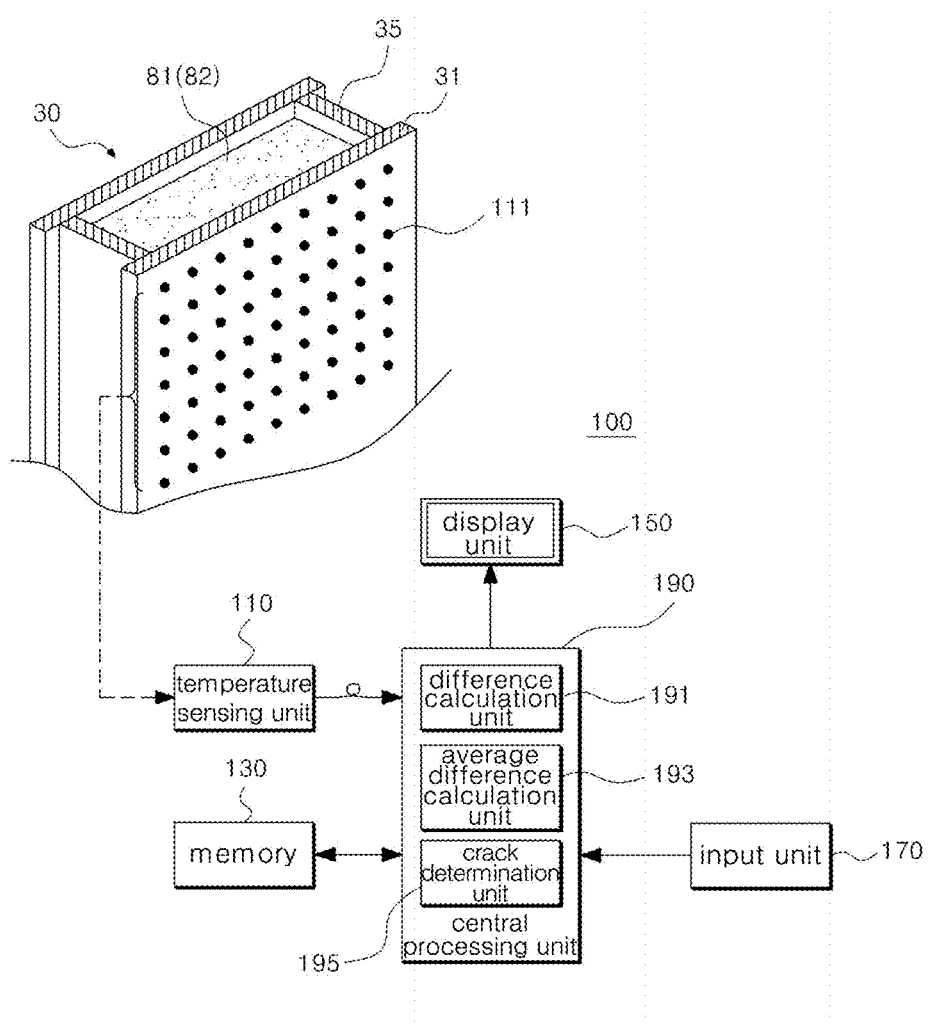
FIG. 25 shows a system for diagnosing cracking in a solidified shell in a mold according to a fourth embodiment of the present invention.

FIG. 25 shows a system for diagnosing cracking in a solidified shell in a mold according to a fourth embodiment of the present invention. As can be seen therein, a crack diagnosis system 100 comprises a temperature sensing unit 110, a memory 130, a display unit 150, an input unit 170 and a processor 190.

The temperature sensing unit 110 comprises a plurality of temperature sensors 111 arranged in a matrix form in the long side 31 of the mold. The plurality of temperature sensors 111 arranged in the mold 30 sense in real-time the temperature of the mold during a continuous casting process. The temperature of the mold 30 is regarded to be the same as that of the solidified shell 81 present in the mold 30.

Herein, the temperature sensors 111 have identification information for identifying the respective regions disposed in the mold 30. Thus, when the temperature of the mold 30 is sensed by each of the temperature sensors 111, the temperature sensing unit 110 transmits the sensed temperature information to the processor 190.

The temperature sensors 111 may be either of thermocouples and temperature sensors.

Figure 26:
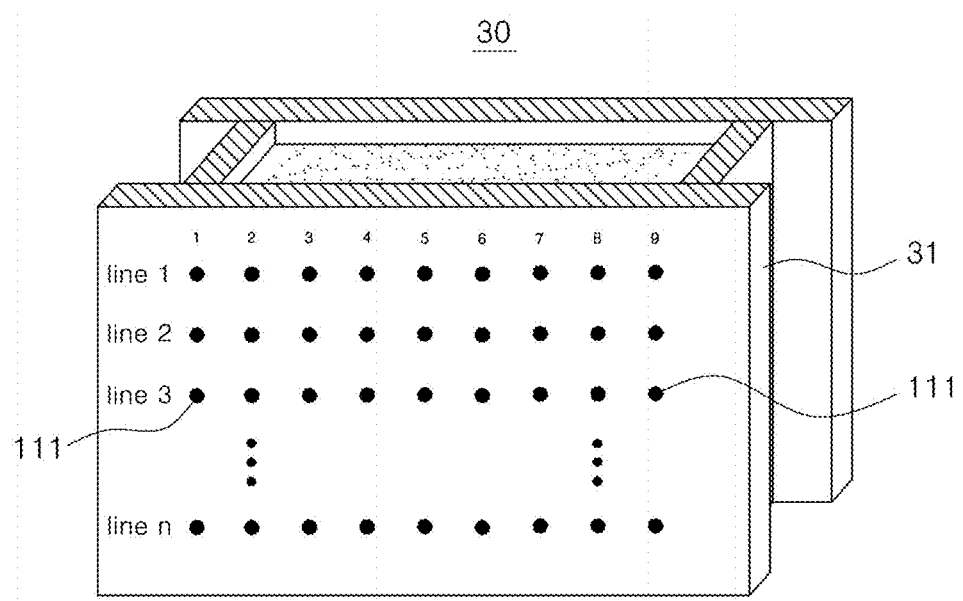
FIG. 26 shows temperature sensors arranged in the long side of a mold according to the present invention.

Although the embodiment of the present invention illustrates nine temperature sensors 111 per line as shown in FIG. 26, the number (N×9) of the temperature sensors 111 can be changed as required. Although FIG. 26 illustrates that the plurality of temperature sensors 111 are arranged throughout the long side 31 of the mold, they may also be selectively arranged at the upper, lower or central portion of the long side 31 of the mold. It should be noted that, when the temperature sensors 111 are arranged throughout the long side 31 of the mold, accuracy for crack detection can be improved.

The memory 130 stores a time period and measurement time for detection of the temperature of the mold 30, an elementary time for measurement, a reference value for determination of occurrence of cracks, and various control programs.

The display unit 150 may display the average value of temperature differences between the maximum temperature and minimum temperature of the temperature sensors of each line as a function of time.

The input unit 170 is configured such that it receives various operating commands or set values from the outside and transmits the received values to the processor 190.

The processor 190 repeatedly acquires the temperature difference between the maximum temperature and minimum temperature of each line from the temperatures, detected from the temperature sensing unit 110, for a set unit time, and uses the average value of the acquired temperature differences to diagnose whether cracking has occurred in the solidified shell 81 that is discharged from the mold 30.

For example, if the temperature sensors 111 are arranged in a matrix of N (lines)×9 (rows) as shown in FIG. 26, the processor 190 extracts the maximum temperature and minimum temperature of each line, repeatedly acquires the temperature difference between the extracted maximum temperature and minimum temperature one or more times, and calculates the average value of the repeatedly acquired temperature differences. Then, the processor 190 compares the acquired average value with a preset reference value, thereby diagnosing whether cracking has occurred in the solidified shell, for each line.

The processor 190 calculates the temperature difference by subtracting the minimum temperature from the maximum temperature for each line, and may temporarily store the calculated temperature difference together with the measurement time information in the memory 130.

The processor 190 may comprise a difference calculation unit 191, an average-difference calculation unit 193 and a crack determination unit 195.

The difference calculation unit 191 acquires each of the maximum temperature and the minimum temperature from the temperatures detected by the temperature sensors of each line of the temperature sensing unit 110, and calculates the temperature difference between the acquired maximum temperature and minimum temperature.

The average-difference calculation unit 193 allows the temperature difference to be repeatedly acquired for a set unit time and calculates the average value of the repeatedly acquired temperature differences. Of course, the average-difference calculation unit 193 may store the periodically acquired temperature differences and the average value of the temperature differences together with the measurement time information in the memory 130.

The crack determination unit 195 compares the calculated average value of the temperature differences with the preset reference value to thereby diagnose whether cracking has occurred in the solidified shell.

The processor 190 may display the average value of the temperature differences, calculated by the average-difference calculation unit 193, on the display 150.

Meanwhile, the processor 190 repeatedly acquires the temperature difference between the maximum temperature and the minimum temperature for each line for a set unit time, and uses the average value of the acquired temperature differences to diagnose whether cracking has occurred in the solidified shell that is discharged from the mold. The processor 190 may repeatedly collect the average value of the acquired temperature differences for a set elementary time, calculate the difference between the maximum value and minimum value of the collected average values and compare the calculated difference with a preset reference value to thereby diagnose whether cracking has occurred in the solidified shell.

Herein, the processor 190 may comprise: the difference calculation unit 191 that acquires each of the maximum temperature and the minimum temperature from the temperatures detected by the temperature sensors of each line of the temperature sensing unit 110 and calculates the temperature difference between the acquired maximum temperature and minimum temperature; the average-difference calculation unit 193 that allows the temperature difference to be repeatedly acquired for a set unit time and calculates the average value of the repeatedly acquired temperature differences; and the crack determination unit 195 that repeatedly acquires the average value of the temperature differences for a set elementary time, calculates the difference between the maximum value and minimum value of the repeatedly acquired average values and compares the calculated difference with a preset reference value to thereby diagnose whether cracking has occurred in the solidified shell.

Figure 27:
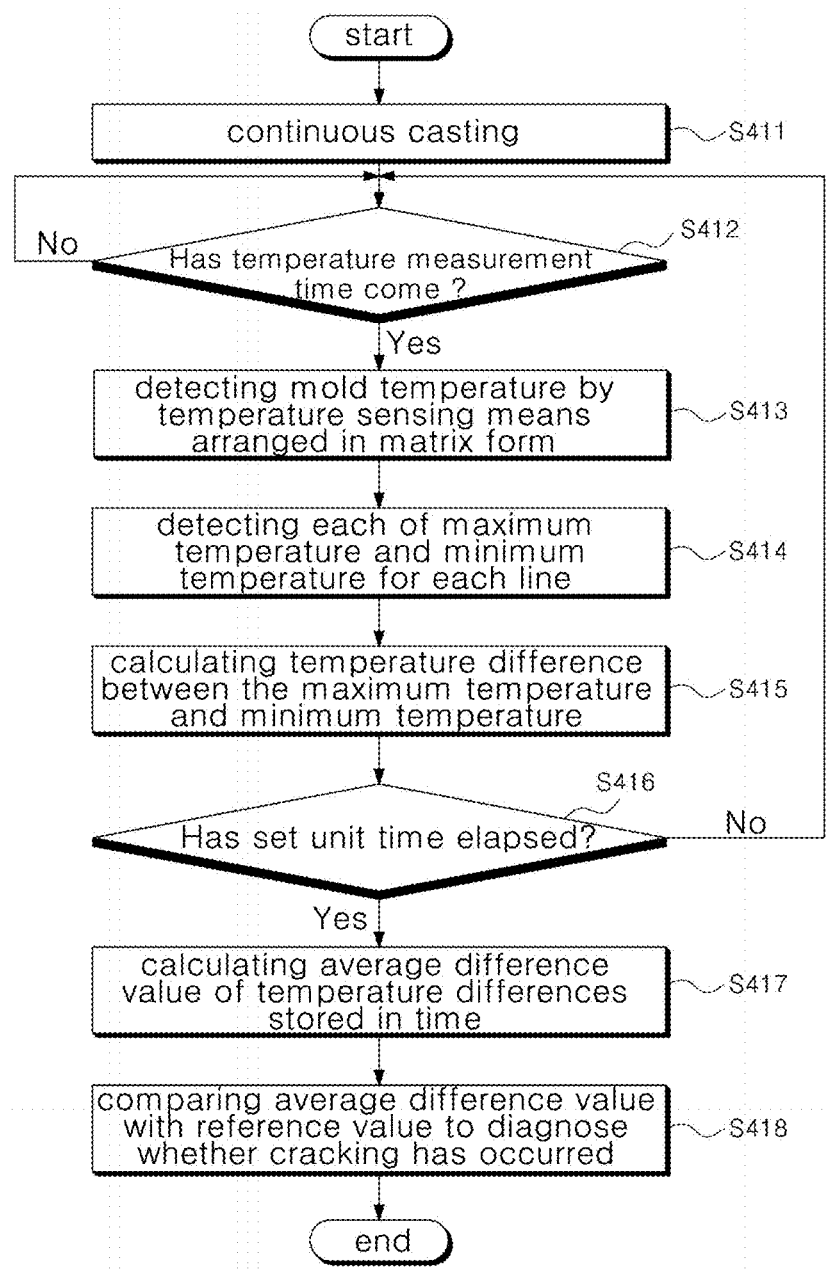
FIG. 27 is a flowchart showing a process for diagnosing cracking in a solidified shell according to one embodiment of FIG. 25.

FIG. 27 is a flowchart showing a process for diagnosing cracking in a solidified shell according to an embodiment of FIG. 25.

As shown in FIG. 27, during a continuous casting process, when the set temperature measurement time is reached, the temperature sensing unit 110 detects in real-time the mold temperature using the temperature sensors arranged in a matrix form in the mold (S411 to S413). Herein, the temperature sensing unit 110 transmits the identification information of each of the temperature sensors 112 together with the temperature information to the processor 190, and from the transmitted identification information, the processor 190 determines the line to which the temperature information belongs.

Then, the processor 190 extracts the maximum temperature and minimum temperature of each line from the detected mold temperatures, calculates the temperature difference between the extracted maximum temperature and minimum temperature, and temporarily stores the calculated temperature difference together with the measurement time information in the memory 130 (S414 and S415). Herein, the processor 190 may display the calculated temperature difference as a function of time on the display unit 150.

Then, the processor 190 determines whether the set unit time (N) has elapsed (S416), and if the set unit time has not elapsed, the above steps (S412 to 5415) are repeated to acquire the temperature difference between the maximum temperature and the minimum temperature of each line again, and the acquired temperature difference together with the measurement time information is temporarily stored in the memory 130.

This process is repeatedly performed for the set unit time (N).

If the set unit time has elapsed (S416), the processor 190 reads the acquired temperature differences from the memory 130, calculates the average value of the temperature differences (S417), and compares the calculated average value of the temperature differences with the preset reference value to thereby diagnose whether cracking has occurred in the solidified shell 81, for each line (S418). If the average value of the temperature differences is greater than the reference value, the processor 190 diagnoses that cracking has occurred in the solidified shell 81.

Figure 28:
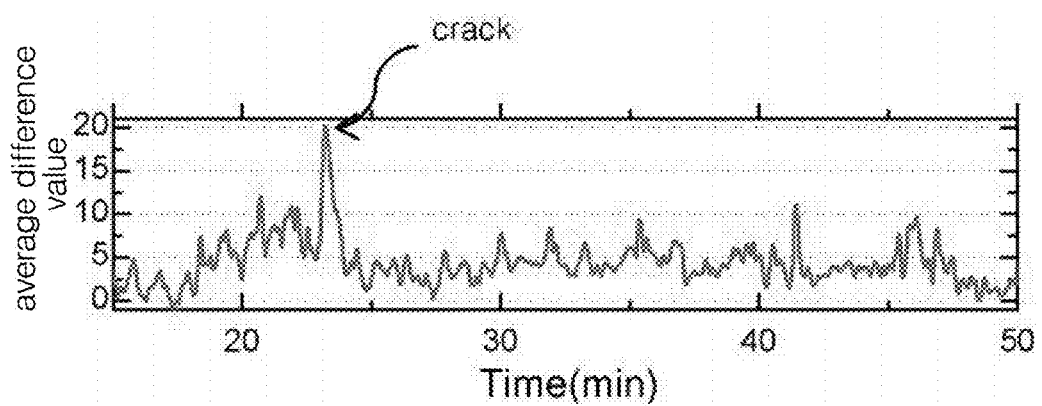
FIG. 28 is a graphic diagram showing the average value of the temperature differences, calculated in FIG. 27, as a function of time.

As shown in FIG. 28, the processor 190 may display the average difference value for any line, calculated per set unit time, on the display unit 150 as a function of time.

In FIG. 28, the y-axis is the average difference value for any line. When the reference value is set at 15, the processor 190 diagnoses that longitudinal cracking has occurred in the solidified shell 81 in the mold 30, if the average difference value is greater than 15. Herein, the reference may differ between the lines in which the temperature sensors 111 are disposed.

The crack diagnosis algorithm according to the present invention shows relatively excellent performance for detection of cracks occurring in each line.

Figure 29:
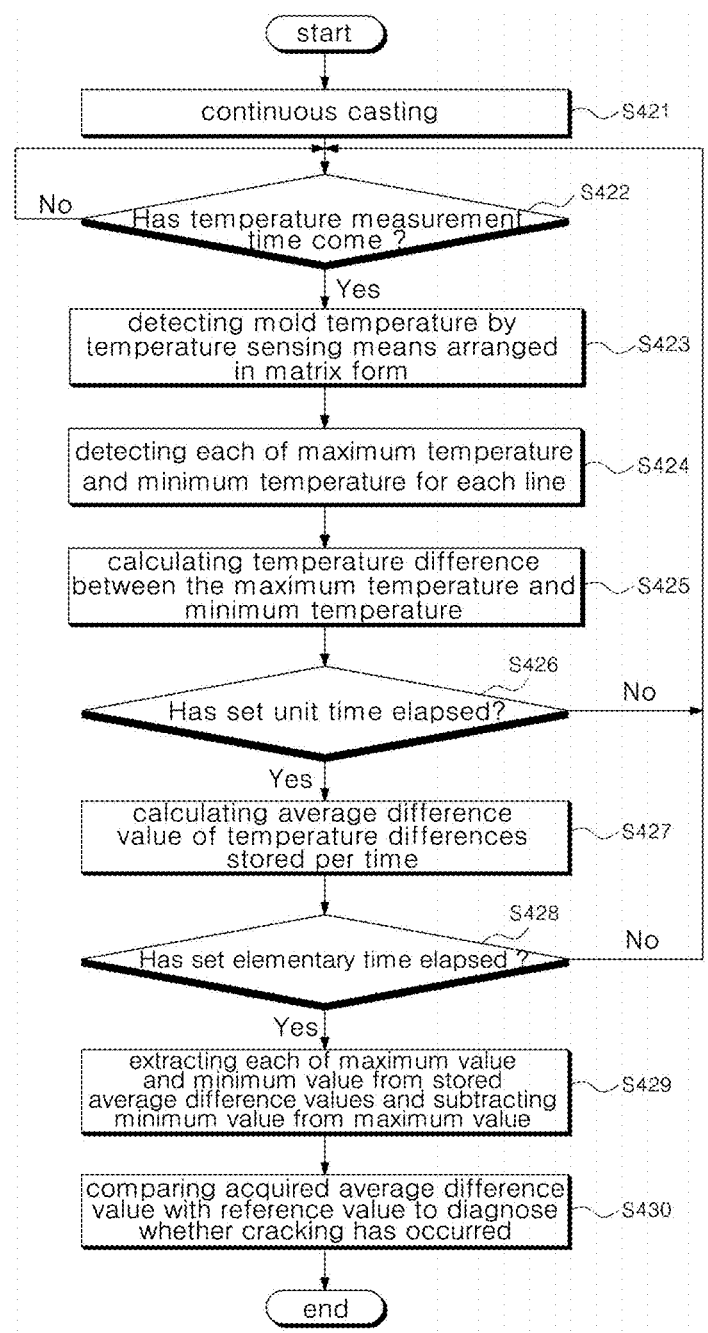
FIG. 29 is a flowchart showing a process for diagnosing cracking in a solidified shell according to another embodiment of FIG. 25.

FIG. 29 is a flowchart showing a process for diagnosing cracking in a solidified shell according to another embodiment of FIG. 25.

As shown in FIG. 25, during a continuous casting process, when the set temperature measurement time is reached, the temperature sensing unit 110 detects in real-time the mold temperature using the temperature sensors arranged in a matrix form in the mold (S421 to S423). Herein, the temperature sensing unit 110 transmits the identification information of each of the temperature sensors 112 together with the temperature information to the processor 190, and from the transmitted identification information, the processor 190 determines the line to which the temperature information belongs.

Then, the processor 190 extracts the maximum temperature and the minimum temperature for each line from the detected mold temperatures, calculates the temperature difference between the extracted maximum temperature and minimum temperature, and temporarily stores the calculated temperature difference together with the measurement time information in the memory (S424 and S425). Herein, the processor 190 may display the calculated temperature difference as a function of time on the display unit 150.

Then, the processor 190 determines whether the set unit time (N) has elapsed (S426), and if the set unit time has not elapsed, the above steps (S422 to 5425) are repeated to acquire the temperature difference between the maximum temperature and the minimum temperature for each line again, and the acquired temperature difference together with the measurement time information is temporarily stored in the memory 150.

This process is repeatedly performed for the set unit time (N).

If the set unit time has elapsed (S426), the processor 190 reads the repeatedly acquired temperature differences from the memory, calculates the average value of the temperature difference and temporarily stores the calculated average difference value in the memory 130 (S427).

Then, the processor 190 determines whether a set elementary time (Te) has elapsed (S428), and if the elementary time (Te) has not elapsed, the above steps (S422 to 5427) are repeatedly performed to repeatedly collect the average value of the temperature differences. Herein, the processor 190 may display the average difference value for each line, acquired per set elementary time, as a function of time on the display unit 150 as shown in FIG. 30.

The processor 190 collects the average difference values for the elementary time (Te), and if the elementary time (Te) has elapsed, the maximum value ($T_{max}$) and minimum value ($T_{min}$) of the collected average difference values are extracted, and the maximum difference is calculated by subtracting the extracted minimum value from the maximum value (S429). Then, the processor 190 compares the maximum difference with a preset reference value to thereby diagnose whether cracking has occurred in the solidified shell (S430). Herein, if the maximum value of the temperature differences is greater than the reference value, the processor 190 diagnoses that cracking has occurred in the solidified shell 81.

Figure 30:
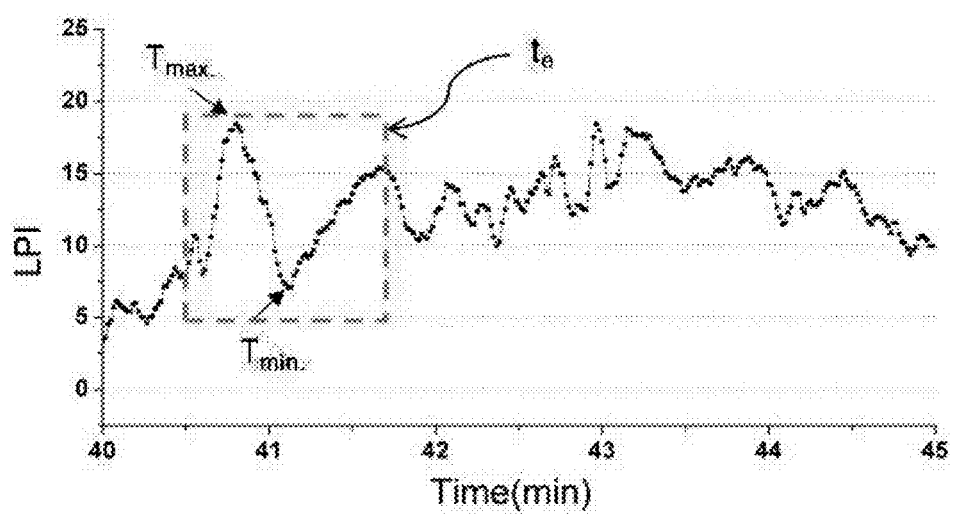
FIG. 30 is a graphic diagram showing the average value of the temperature differences, calculated in FIG. 29, as a function of time.

In FIG. 30, the y-axis is a longitudinal probability index (LPI) which is the average difference value for any line, calculated per unit time (N), and the x-axis is the time axis.

In general, the length of the continuously cast steel 80 that is drawn from the mold 30 may be about 0.9-2.3 m per min, and based on this length, the elementary time (Te) may be set in the range from 15 sec to 180 sec. If the elementary time (Te) is shorter than 15 sec, large cracks cannot be detected, and if the elementary time (Te) is longer than 180 sec, a temperature difference having no connection with cracks can be detected, resulting in a decrease in accuracy.

Herein, the unit time (N) and the elementary time (Te) are information of different references, and the elementary time (Te) is set at a greater value than the unit time (N).

As described above, in the present invention, longitudinal cracking is diagnosed based on the variation in temperature of a solidified shell that is produced in a continuous casting process, so that only the surface of a slab in which longitudinal cracking has occurred can be scarfed, thus reducing the cost for correcting slabs. In particular, in the present invention, cracking occurring at positions corresponding to the temperature sensors of the second group can be more accurately detected.

Figure 31:
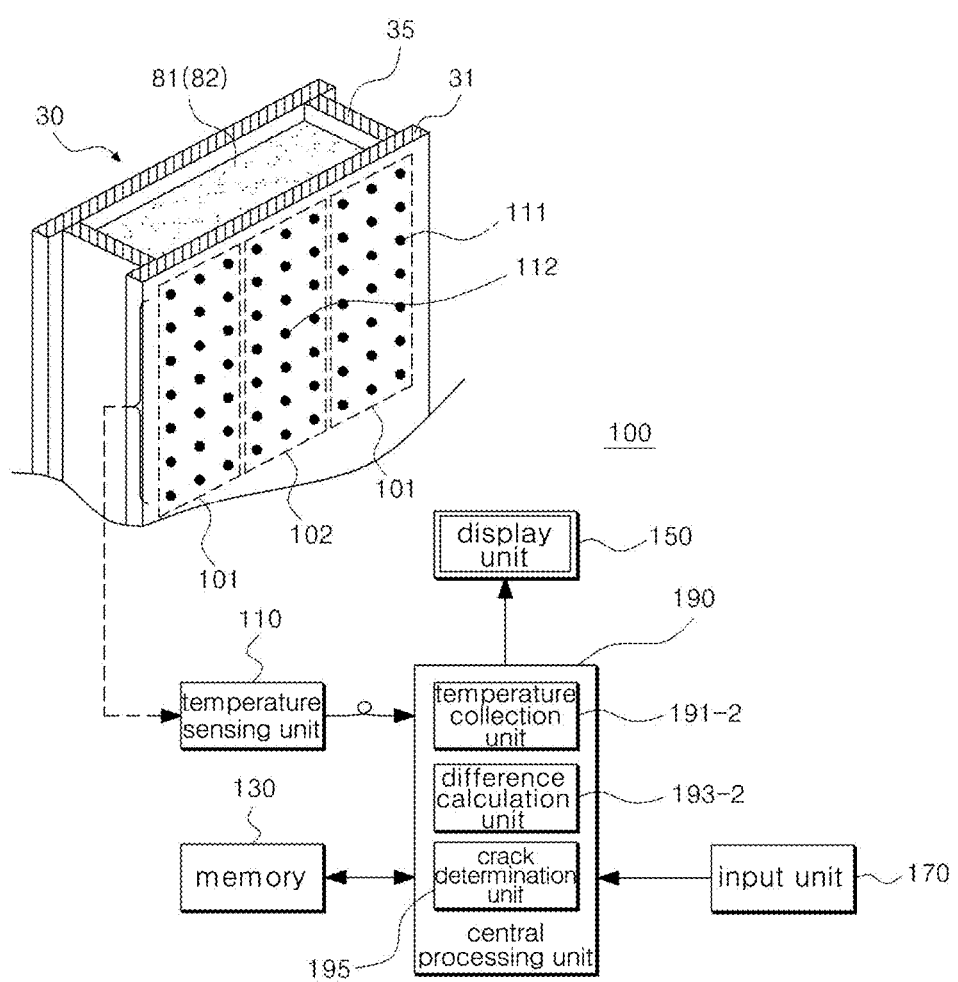
FIG. 31 shows a system for diagnosing cracking in a solidified shell in a mold according to a fifth embodiment of the present invention.

FIG. 31 shows a system for diagnosing cracking in a solidified shell in a mold according to a fifth embodiment of the present invention. As shown therein, a crack diagnosis system 100 comprises a temperature sensing unit 110, a memory 130, a display unit 150, an input unit 170 and a processor 190.

The temperature sensing unit 110 comprises a plurality of temperature sensors 111 and 112 arranged in a matrix form in the long side 130 of the mold. The plurality of temperature sensors 111 and 112 arranged in the mold sense in real-time the temperature of the mold 30 during a continuous casting process. The temperature of the mold 30 is regarded to be the same as that of the solidified shell present in the mold 30.

The temperature sensors 111 and 112 have identification information for identifying the respective regions arranged in the mold 30. Thus, if the temperature of the mold 30 is sensed by each of the temperature sensors 111 and 112, the temperature sensing unit 110 transmits the sensed temperature information to the processor 190.

Figure 32:
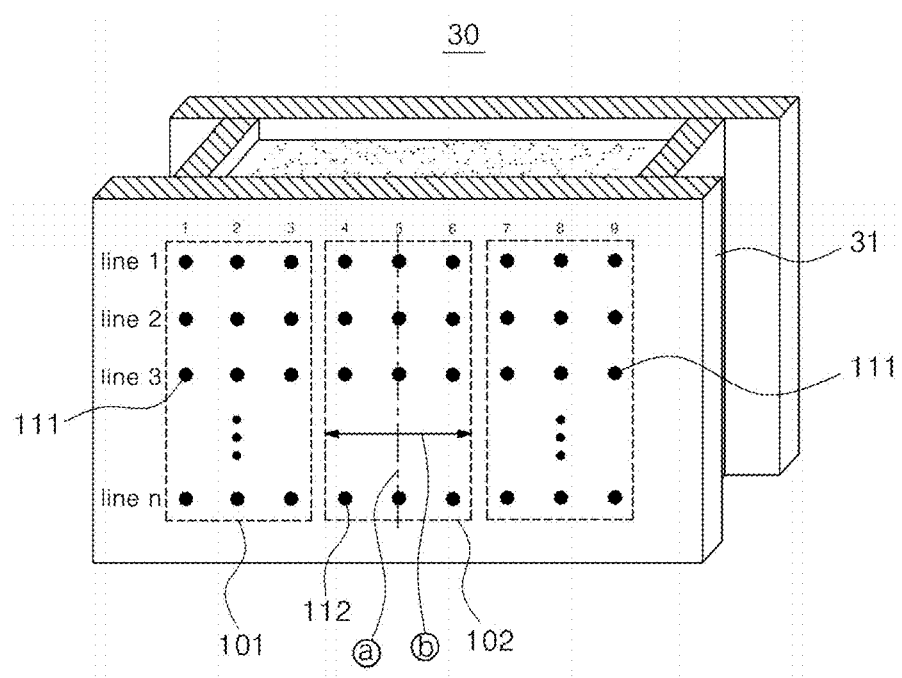
FIG. 32 shows temperature sensors arranged in the long side of a mold according to the present invention.

As shown in FIG. 32, the temperature sensors 111 and 112 of the temperature sensing unit 110 are arranged and embedded in the long side 31 of the mold. The temperature sensors 111 and 112 may be either of thermocouples and temperature sensors.

The plurality of temperature sensors 111 and 112 arranged in the mold 30 are divided into a first group 101 and a second group 102 with respect to a region in which cracking can occur. Generally, cracking occurs in the central portion of the long side 31 of the mold. As shown in FIG. 32, the temperature sensors 112 belonging to the second group 102 are disposed in the central portion of the mold 30, and the temperature sensors 111 belonging to the first group 101 are disposed in both edges of the mold 31. The first group 101 includes at least one temperature sensors disposed in the region in which no cracking occurs, and the second group 102 includes at least one temperature sensors 112 disposed in the region in which cracking occurs. Although the embodiment of the present invention illustrates that the first group 101 includes six temperature sensors 111 per line and the second group 102 includes three temperature sensors 112 per line, the number of the temperature sensors 111 and 112 may be changed as required. If necessary, only the temperature sensors 112 of the second group 102 may be disposed in the mold 30.

The temperature sensors 112 belonging to the second group 102 are located at each of both sides of the central vertical line ⓐ of the mold 30, which is an area corresponding to 15% or less of the width of the mold 30. In other words, the second group 102 is located in the central portion of the long side 31 of the mold, which is a region ⓑ corresponding to about 30% of the width of the long side 31.

FIG. 32 illustrates that the plurality of temperature sensors 111 and 112 are arranged throughout the long side 31 of the mold, but if necessary, only the temperature sensors 112 of the second group 102 may be provided or the temperature sensors 111 and 112 may also be selectively arranged at the upper, lower or central portion of the long side 31 of the mold. It should be noted that, when the temperature sensors 111 and 112 are arranged throughout the long side 31 of the mold, accuracy for crack detection can be improved.

The memory 130 stores a time period and unit time for detection of the temperature of the mold 30, a reference value for determining the occurrence of cracks, and various control programs.

The display unit 150 may display the measured temperature collected by each temperature sensors of the second group, or the temperature difference between the maximum temperature immediately before the temperature decreases and the minimum temperature after the temperature has decreased, for each temperature sensors, as a function of time. The display unit 150 may graphically display the change in the temperature difference.

The input unit 170 is configured such that it receives various operating commands or set values and transmits the received values to the processor 190.

The processor 190 collects the mold temperature from the temperature sensors 112 of the second group 102 for a set unit time, calculates the temperature difference between the maximum temperature immediately before the temperature decreases and the minimum temperature after the temperature has decreased, from the collected mold temperatures for each temperature sensors 112, and uses the maximum temperature difference among the calculated temperature differences to diagnose whether cracking has occurred in the solidified shell in the mold. Herein, the mold temperature is collected only from the temperature sensors 112 of the second group 102.

For example, the temperature sensors 111 and 112 may be arranged in a matrix of N (lines)×9 (rows) as shown in FIG. 32, but the processor collects the mold temperature from the temperature sensors 112 of the second group 102 located at each of both sides of the central vertical line ⓐ of the mold 30, which is an area corresponding to 15% or less of the width of the mold 30.

In other words, the processor 190 periodically collects the sensed temperature information from the temperature sensors 112, arranged in rows 4, 5 and 6 of the long side 31 of the mold, for a set unit time, and stores the collected temperature information in the memory. If the set unit time has elapsed, the processor 190 calculates the temperature difference between the maximum temperature immediately before the temperature decreases and the minimum temperature after the temperature decreased, from the collected mold temperature for each temperature sensors 112, and compares the maximum temperature difference among the calculated temperature differences with a set reference value to thereby diagnose whether cracking has occurred in the solidified shell 81.

The processor 190 may comprise a temperature collection unit 191-2, a difference calculation unit 193-2 and a crack determination unit 195.

The temperature collection unit 191-2 periodically collects the mold temperatures measured by the temperature sensors 112 of the second group 102 for a set unit time, and stores the collected temperatures in the memory 130.

The difference calculation unit 193-2 calculates the temperature difference between the maximum temperature immediately before the temperature decreases and the minimum temperature after the temperature has decreased, from the collected temperatures for each temperature sensors. Of course, the difference calculation unit 193-2 temporarily stores the calculated temperature difference for each temperature sensors in the memory 130.

The crack determination unit 195 compares the maximum temperature difference among the temperature differences, calculated by the difference calculation unit 193-2 for each temperature sensors, with a preset reference value, to thereby diagnose whether cracking has occurred in the solidified shell corresponding to each temperature sensors 112.

The processor 190 may display on the display unit 150 the temperature differences for each temperature sensors 112, calculated by the difference calculation unit 193.

In general, the length of the continuously cast steel 80 that is drawn from the mold 30 may be about 0.9-2.3 m per min, and based on this length, the elementary time (Te) may be set in the range from 15 sec to 180 sec. If the elementary time (Te) is shorter than 15 sec, large cracks cannot be detected, and if the elementary time (Te) is longer than 180 sec, a temperature difference having no connection with cracks can be detected, resulting in a decrease in accuracy. The crack diagnosis system according to the present invention is preferably operated within a time in which casting conditions, including casting velocity, the kind of mold powder, the quantity of cooling water for the mold, and the like, do not change.

Figure 33:
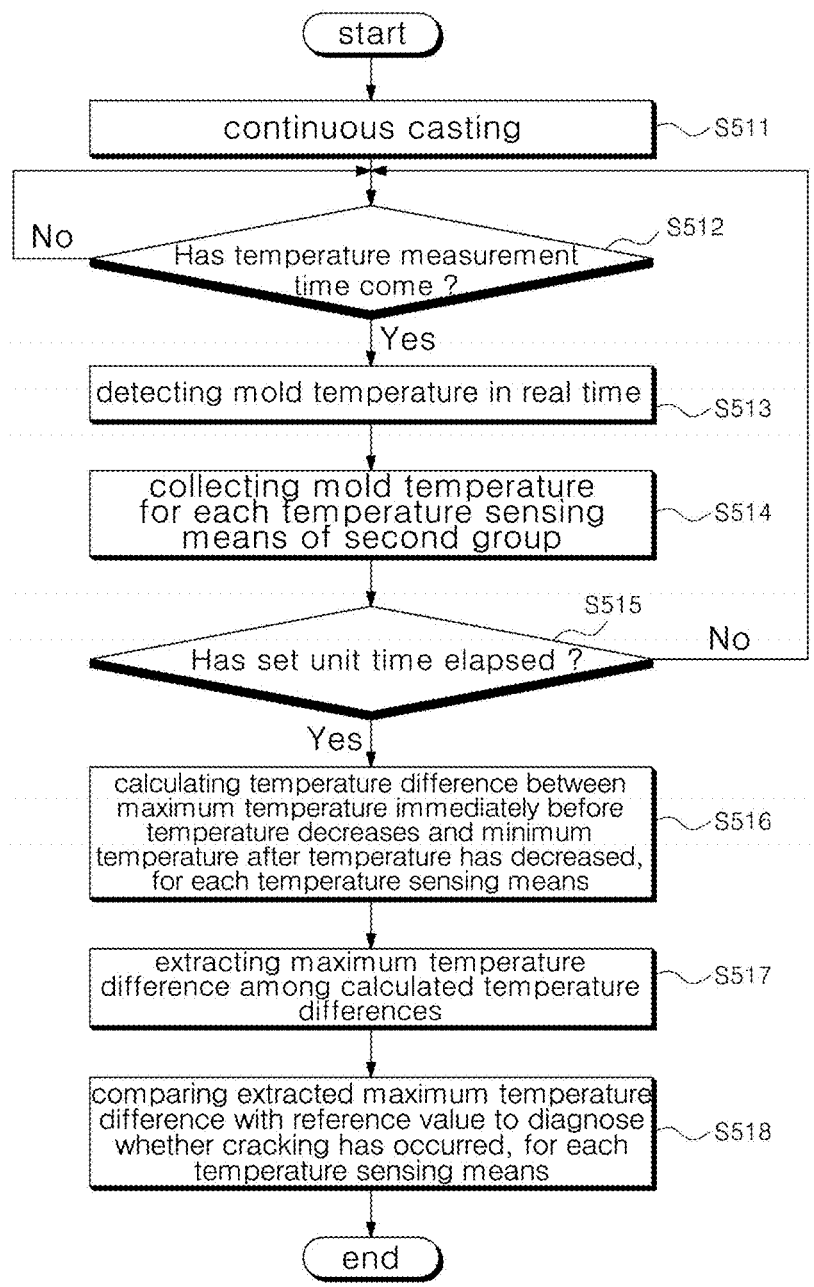
FIG. 33 is a flowchart showing a process for diagnosing cracking in a solidified shell according to an embodiment of FIG. 31.

FIG. 33 is a flowchart showing a process for diagnosing cracking in a solidified shell according to an embodiment of FIG. 31.

As shown in FIG. 31, during a continuous casting process, when the set temperature measurement time is reached, the processor 190 detects in real-time the mold temperature by the temperature sensors 110 (S511 to S513). Herein, the mold sensing means 112 of the second group sense in real-time the mold temperatures in the respective regions arranged in the mold and transmits the sensed temperatures to the processor 190 through the temperature sensing unit. The temperature sensing unit 110 transmits the identification information of each of the temperature sensors 112 together with the temperature information to the processor 190.

The temperature sensors 112 of the second group 102 are disposed in the central portion of the long side 31 of the mold, in which cracking occurs, and they are located at each of both sides of the central vertical line of the mold 30, which is an area corresponding to 30% of the width of the mold 30. As can be seen in FIG. 7, the temperature of the mold 30 differs between the positions of the mold, and particularly, the second group 102 located in the central portion of the mold 30 shows a significant change in the temperature.

As described above, the processor 190 periodically and repeatedly collects the temperature information of the temperature sensors 112 of the second group 102 and stores the collected temperature information together with the time information in the memory 130.

Figure 34:
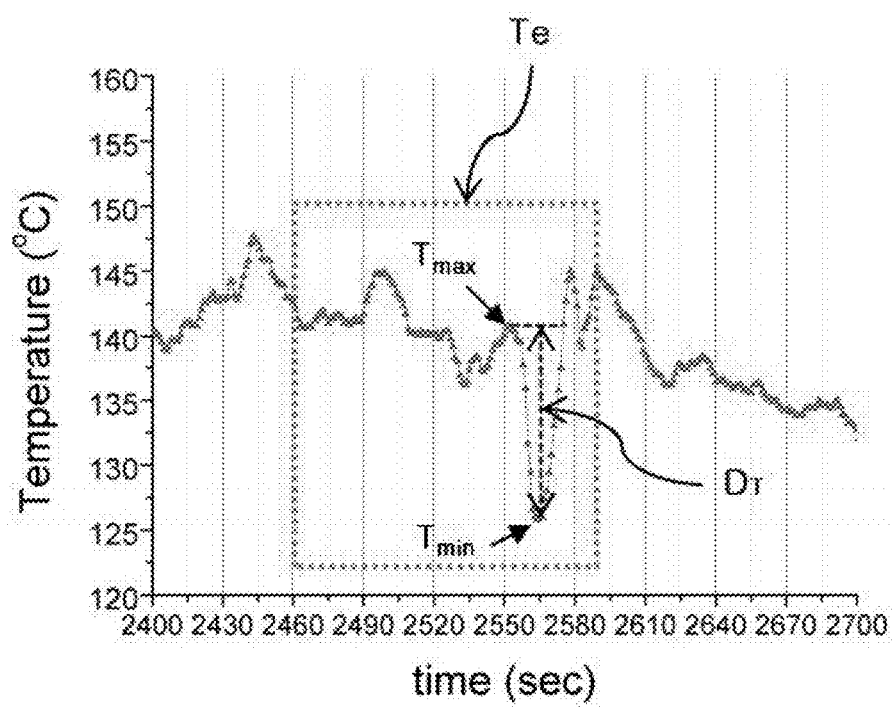
FIG. 34 is a graphic diagram showing the average value of the temperature differences, calculated in FIG. 33, as a function of time.

Then, the processor 190 determines whether the set unit time has elapsed (S515), and if the set unit time has not elapsed, the above steps (S512 to 5514) are repeated to collect the mold temperature. Herein, the unit time may be set in the range from 15 sec to 180 sec. As shown in FIG. 34, the processor 190 may display the measurement temperature of each of the temperature sensors 112, calculated per unit time, as a function of time on the display unit 150.

As the set elementary time (Te) has elapsed (S515), as shown in FIG. 34, the processor 190 calculates the temperature difference ($D_T$) between the maximum temperature ($T_{max}$) before the temperature decreases and the minimum temperature ($T_{min}$) after the temperature decreased, from the mold temperatures stored the memory 130, for each temperature sensors 112. Thus, for each temperature sensors 112, a plurality of the temperature differences ($D_T$) will be calculated.

Figure 35:
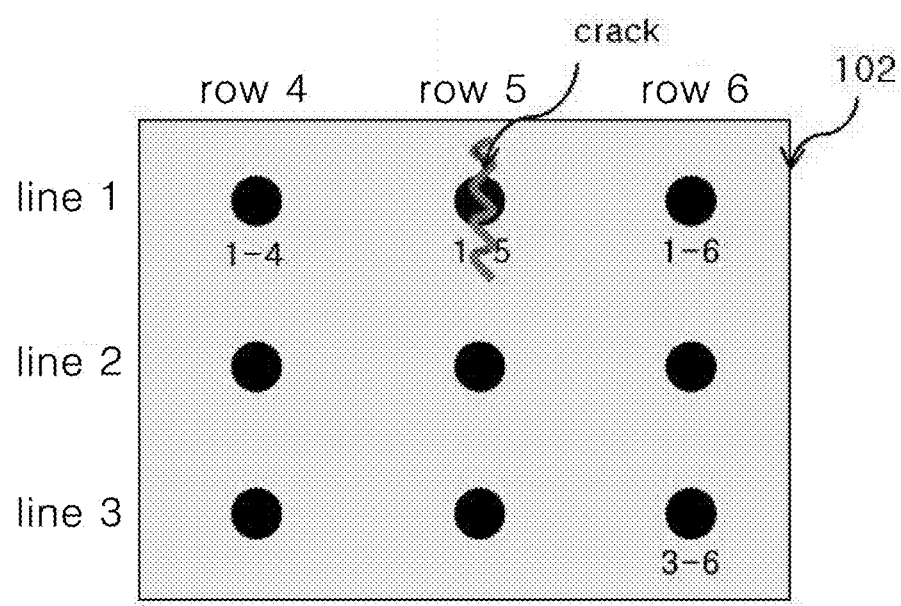
FIG. 35 shows cracking in a mold.

Then, the processor 190 extracts the maximum temperature difference for each temperature sensors 112 from the calculated temperature differences and compares the extracted maximum temperature difference with a preset reference value to thereby determine whether cracking has occurred in the solidified shell corresponding to each temperature sensors 112, as shown in FIG. 35.

If the maximum temperature difference among the mold temperatures acquired by the second temperature sensors 1-5 of the temperature sensors 1-4 to 3-6 located in the second group 102 is greater than the reference value, as shown in FIG. 35, the processor 190 determines that longitudinal cracking has occurred in the solidified shell corresponding to the second temperature sensors 1-5. Herein, the reference value may differ between the lines and rows of the temperature sensors 112.

This crack diagnosis algorithm shows relatively excellent performance for detecting cracking occurring in positions corresponding to the temperature sensors 112 of the second group 102 as shown in FIG. 35.

As described above, in the present invention, longitudinal cracks are diagnosed based on the variation in temperature of a solidified shell that is produced in a continuous casting process, so that only the surface of a slab in which longitudinal cracks have occurred can be scarfed, thus reducing the cost for correcting slabs. In particular, in the present invention, cracks occurring at positions corresponding to the temperature sensors of the second group can be more accurately detected.

Figure 36:
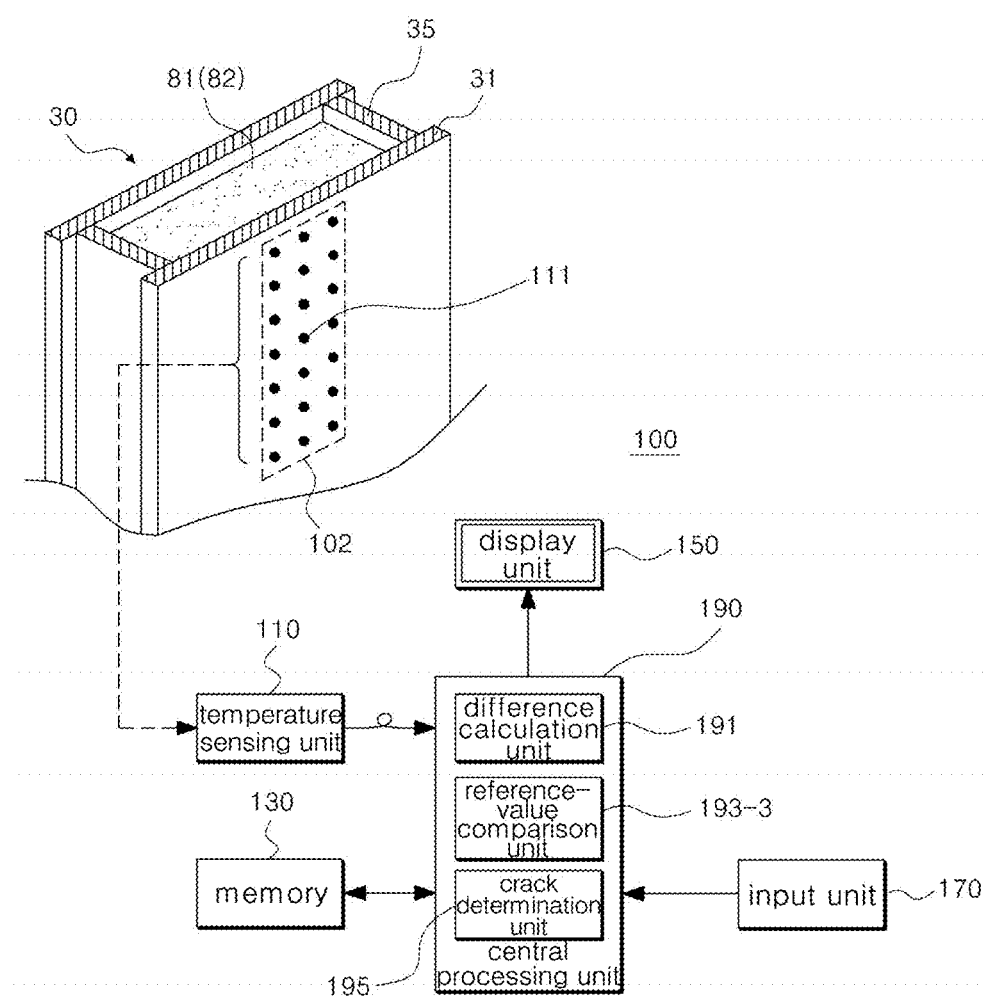
FIG. 36 shows a system for diagnosing cracking in a solidified shell in a mold according to a sixth embodiment of the present invention.

FIG. 36 shows a system for diagnosing cracking in a solidified shell in a mold according to a sixth embodiment of the present invention. As shown therein, a crack diagnosis system 100 comprises a temperature sensing unit 110, a memory 130, a display unit 150, an input unit 170 and a processor 190.

The temperature sensing unit 100 comprises a plurality of temperature sensors 111 arranged in a matrix form in the central portion of the long side 31 of the mold. The plurality of temperature sensors 111 arranged in the mold 30 sense in real-time the temperature of the mold 30 during a continuous casting process. The temperature of the mold 30 is regarded to be the same as that of the solidified shell 81 present in the mold 30.

The temperature sensors 111 have identification information for identifying the respective regions arranged in the mold 30. Thus, if the temperature of the mold 30 is sensed by the temperature sensors 111, the temperature sensing unit 110 transmits the sensed temperature information to the processor 190.

Figure 37:
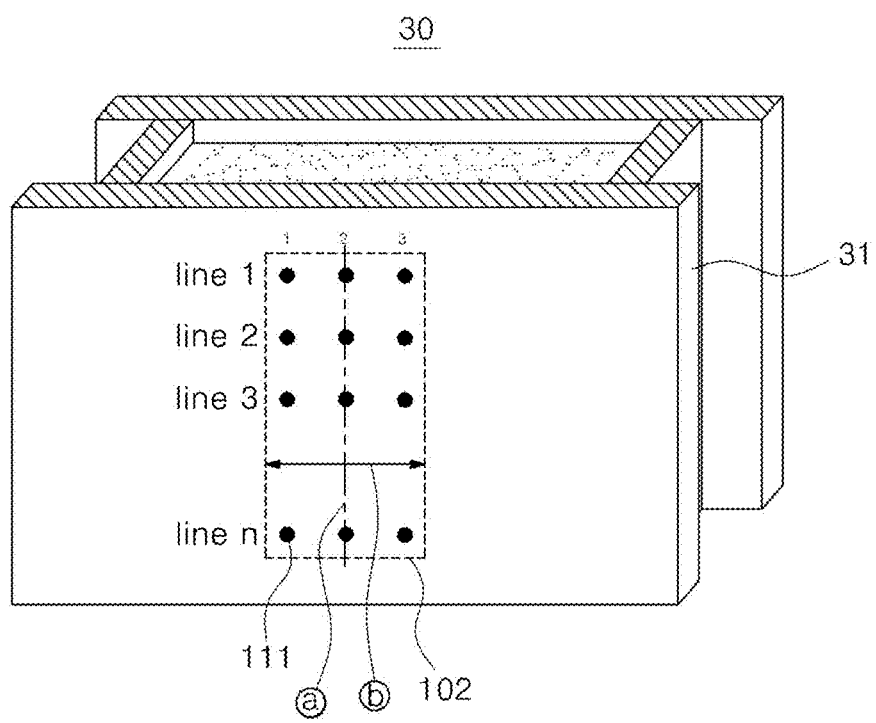
FIG. 37 shows temperature sensors arranged in the long side of a mold according to the present invention.

As shown in FIG. 37, the temperature sensors 111 of the temperature sensing unit 110 are arranged and embedded in the central portion 102 of the long side 31 of the mold in a matrix of N (lines)×3 (rows). The temperature sensors 111 may be either of thermocouples and temperature sensors 111.

The plurality of temperature sensors 111 arranged in the mold 30 are provided in a region of the mold, in which cracking in the solidified shell can occur. Generally, cracking occurs in the central portion of the long side 31 of the mold. Although the embodiment of the present invention illustrates three temperature sensors 111 per line, the number of the temperature sensors 111 may be changed as required.

The temperature sensors 111 disposed in the central portion of the mold 30 are located at each of both sides of the central vertical line ⓐ of the mold 30, which is an area corresponding to 15% or less of the width of the mold 30. In other words, the temperature sensors 111 are located in the central portion of the long side 31 of the mold, which is a region ⓑ corresponding to about 30% of the width of the long side 31.

Although FIG. 37 illustrates that the plurality of temperature sensors 111 are arranged throughout the central portion 102 of the long side 31 of the mold, they may, if necessary, be selectively arranged at the upper, lower or central portion of the long side 31 of the mold. It should be noted that, when the temperature sensors 111 are arranged throughout the central portion of the long side 31 of the mold, accuracy for crack detection can be improved.

The memory 130 stores a time period and unit time for detection of the temperature of the mold 30, a reference value for determining the occurrence of cracks, casting conditions, reference conditions, the temperature and time of measurement by each temperature sensors 111, and various control programs.

The display unit 150 may display the measurement temperature collected by each temperature sensors 111 of the second group 102, or the temperature difference between the maximum temperature before the temperature decreases and the minimum temperature after the temperature decreased, for each temperature sensors 111, as a function of time. The display unit 150 may graphically display the change in the temperature difference.

The input unit 170 is configured such that it receives various operating commands or set values and transmits the received values to the processor 190.

The processor 190 collects the mold temperature through the temperature sensing unit 110, stores visual information on the maximum temperature and the minimum temperature for each temperature sensors 111 when the temperature difference between the maximum temperature immediately before the temperature decreases and the minimum temperature after the temperature decreased is greater than a preset reference value, and uses the visual information of the temperature sensors 111 belonging to the same row among the stored visual information to diagnose whether cracking has occurred in the solidified shell.

In other words, the processor 190 uses visual information for at least two temperature sensors 111 belonging to the same row to diagnose whether cracking has occurred. Specifically, the processor 190 uses the visual information of the temperature sensors 111 belonging to the same row to calculate the interline movement time of the temperature difference, and determines whether the calculated movement time falls within the range of set reference conditions to thereby diagnoses whether cracking has occurred in the solidified shell.

The processor 190 may comprise a difference calculation unit 191, a reference-value comparison unit 193-3 and a crack determination unit 195.

The difference calculation unit 191 collects in real-time the mold temperature through the temperature sensing unit 110, stores the collected mold temperature together with the visual information in the memory 130, and calculates the temperature difference between the maximum temperature immediately before the temperature decreases and the minimum temperature after the temperature has decreased, from the stored mold temperatures for each temperature sensors 111. Of course, the difference calculation unit 191 temporarily stores the calculated temperature difference for each temperature sensors 111 in the memory 130.

The reference-value comparison unit 193-3 compares the calculated temperature difference with the set reference value, and if the temperature difference is greater than the reference value, the comparison unit 193-3 stores visual information for the maximum temperature immediately before the temperature of the relevant temperature sensors 111 decreases and the minimum temperature after the temperature has decreased, in the memory 130.

The crack determination unit 195 uses the visual information of the temperature sensors 111 belonging to the same row to calculate the interline movement time of the temperature difference and determines whether the calculated movement time falls within the set reference condition range to thereby diagnose whether cracking has occurred in the solidified shell.

The reference conditions include the time obtained by dividing the interline spacing of the temperature sensors 111 by casting velocity. Specifically, the reference conditions may include a first reference value obtained by dividing the interline spacing of the temperature sensors 111 by casting velocity and subtracting the set offset time from the divided value, and a second reference value obtained by dividing the interline spacing of the temperature sensors 111 by casting velocity and adding the set offset time to the divided value. Herein, if the calculated interline movement time is between the first reference value and the second reference value, the processor 190 diagnoses that cracking has occurred.

Generally, the movement speed of continuously cast steel in the mold is at least 15 cm per 10 sec, the offset time may be set in the range from 1 sec to 2 sec, and the reference value may be set in the range from 8 to 12° C. If the casting velocity is higher than 0.9 m/min, the offset time may be increased or decreased. Also, the temperature of the mold 30 can be changed. Generally, it is slightly changed when the level of molten steel changes or mold powder is introduced. If the reference value is lower than 8° C., there is a conventional change as described above, and if the reference value is greater than 8° C., there is a high possibility for defects to occur in the solidified shell 81. If the reference value is set at an excessively high value, cracking in the solidified shell cannot be accurately detected. Thus, the reference value is preferably set between 8 and 12° C. Of course, the reference value may also be changed depending on equipment.

The crack diagnosis system according to the present invention is preferably operated within a time in which casting conditions, including the interline spacing of the temperature sensors 111, casting velocity, the kind of mold powder, the quantity of cooling water for the mold, and the like, do not change.

Figure 38:
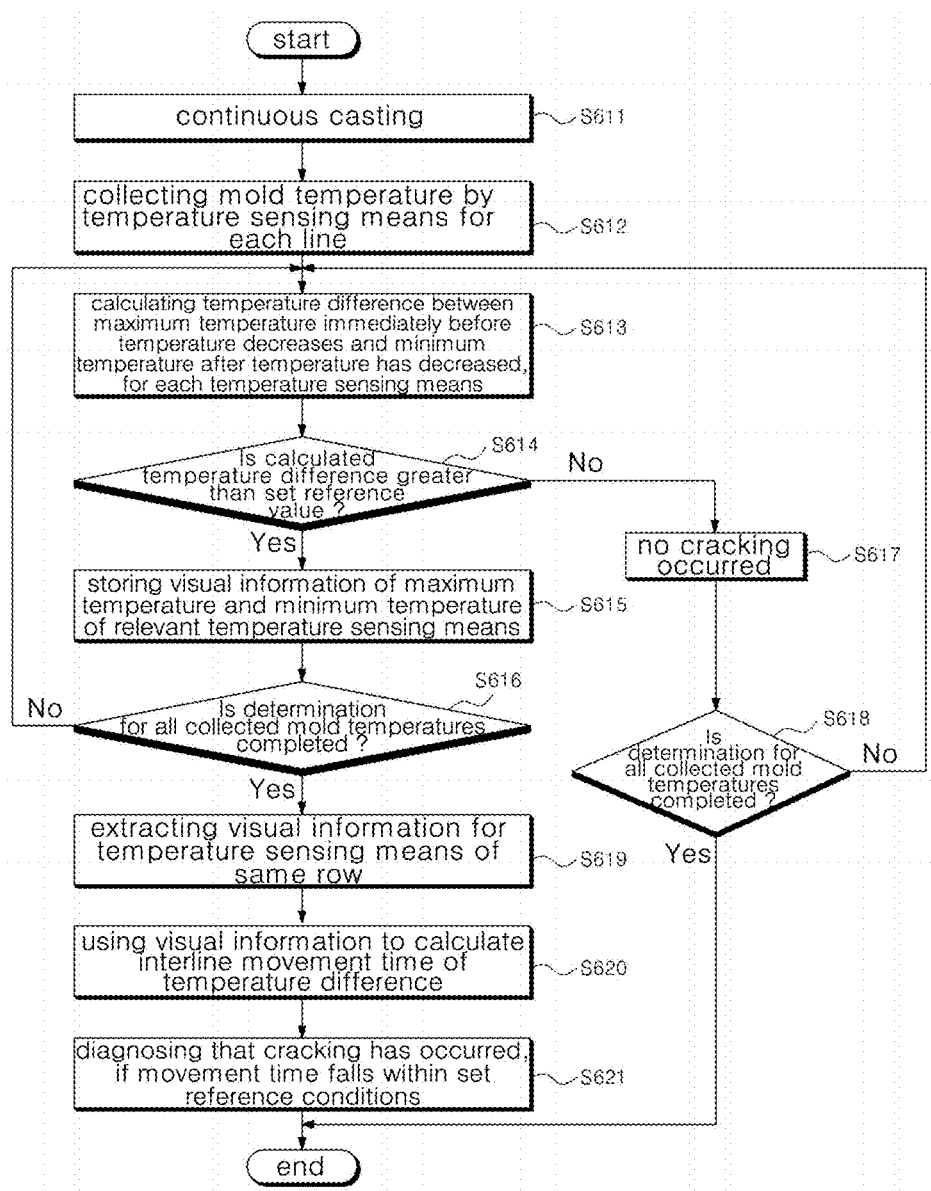
FIG. 38 is a flowchart showing a process for diagnosing cracking in a solidified shell according to an embodiment of FIG. 36.

FIG. 38 is a flowchart showing a process for diagnosing cracking in a solidified shell according to an embodiment of FIG. 36.

As shown in FIG. 38, during a continuous casting process, when the set temperature measurement time is reached, the processor 190 detects in real-time the mold temperature through the temperature sensing unit 110 and stores the detected temperature in the memory (S611 and S612). Herein, the temperature sensors 111 sense the mold temperature of the regions in which they are disposed, and transmit the sensed temperature to the processor 190 through the temperature sensing unit. The temperature sensing unit 110 transmits the identification information of the temperature sensors 111 together with the temperature information to the processor 190.

The temperature sensors 111 are disposed in the central portion of the long side 31 of the mold, in which cracking occurs, and they are located at each of both sides of the central vertical line of the mold 30, which is an area corresponding to 15% or less of the width of the mold 30.

Figure 39:
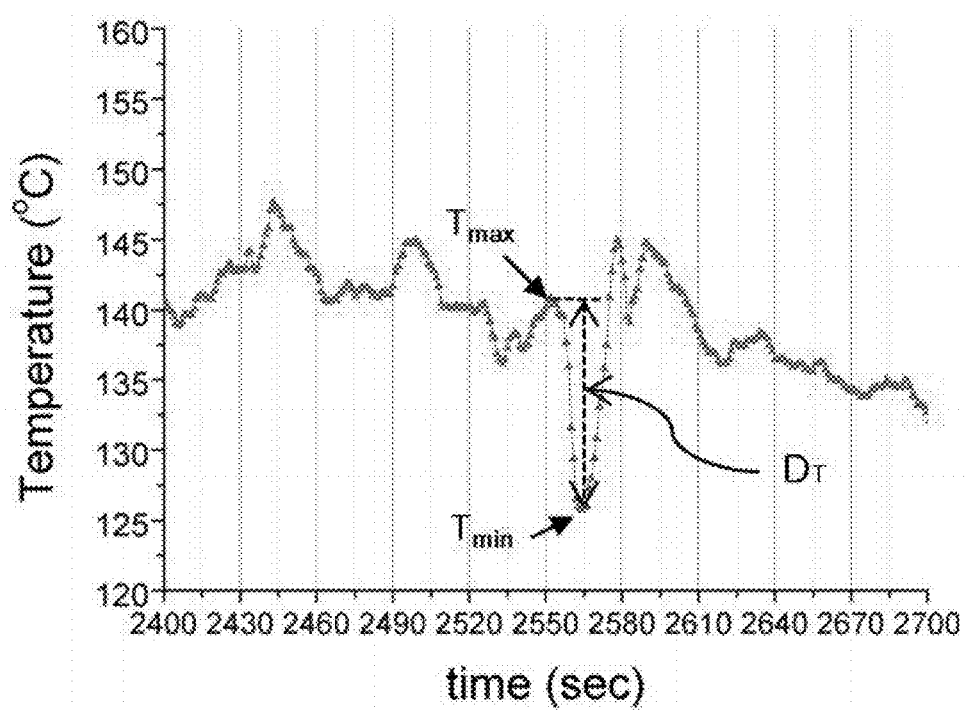
FIG. 39 is a graphic diagram showing the temperatures, measured by any temperature sensor unit, as function of time.

The processor 190 periodically and repeatedly collects temperature information for the temperature sensors 111 present in the region in which cracking occurs, and stores the collected temperature information together with the time information in the memory 130. As shown in FIG. 39, the processor 190 may display the temperatures, measured by the temperature sensors 111, as a function of time on the display unit 150.

If a specific time has elapsed, as shown in FIG. 39, the processor 190 uses the mold temperatures, stored in the memory 130, to calculate the temperature difference ($D_T$) between the maximum temperature ($T_{max}$) immediately before the temperature decreases and the minimum temperature ($T_{min}$) after the temperature has decreased, for each temperature sensors 111 (S613). Thus, one or more temperature differences ($D_T$) will be calculated for each temperature sensors 111.

The processor 190 compares the calculated temperature difference ($D_T$) with a preset reference value to determine whether the temperature difference ($D_T$) is greater than the reference value (S614), and if the temperature difference is greater than the reference value, the time corresponding to the maximum temperature ($T_{max}$) immediately before the temperature of the relevant temperature sensors 111 decreases and the time corresponding to the minimum temperature ($T_{min}$) after the temperature has decreased, together with the information of the temperature sensors 111, are stored in the memory 130 (S615). The reference value may be set in the range from 8 to 12° C.

Then, the processor 190 checks whether the calculation of the temperature difference for all the collected mold temperatures for each temperature sensors 111 and determination for whether the temperature difference is greater than the reference value are completed (S616), and if these operations are not completed, the processor 190 continues to calculate the temperature difference for the next temperature sensors 111 (S613).

Meanwhile, if the temperature difference calculated in step (S614) is not greater than the set reference value, the processor 190 determines that no cracking has occurred in the relevant temperature sensors 111 (S617). Then, the processor 190 checks whether the calculation of the temperature difference for all the collected mold temperatures for each temperature sensors 111 and determination for whether the temperature difference is greater than the reference value are completed (S618), and if these operations are not completed, the processor 190 continues to calculate the temperature difference for the next temperature sensors 111 (S613).

If step (S616) indicates that the calculation of the temperature difference for all the collected mold temperatures for each temperature sensors 111 and determination for whether the temperature difference is greater than the reference value are completed, the processor 190 extracts visual information for the temperature sensors belonging to the same row (S619). The processor 190 uses the visual information of the temperature sensors 111 of the same row to calculate the interline movement time of the temperature difference (S620), and determines whether the calculated movement time falls within the set reference condition range to thereby diagnoses whether cracking has occurred in the solidified shell (S621).

Herein, the reference conditions may include the time obtained by dividing the interline spacing of the temperature sensors by casting velocity. Specifically, as shown in the following equation 1, the reference conditions include a first reference value $$\left(\frac{Dn}{Vc} - \beta\right)$$

obtained by dividing the interline spacing (Dn) of the temperature sensors 111 by casting velocity (Vc) and subtracting the set offset time (β) from the divided value, and a second reference value $$\left(\frac{Dn}{Vc} + \beta\right)$$

obtained by dividing the interline spacing (Dn) of the temperature sensors 111 by casting velocity (Vc) and adding the set offset time (β) to the divided value. Herein, the offset time (β) may be set at 1 to 2 sec in view of casting velocity.

The processor 190 determines whether the calculated interline movement time ($t(n)_{max} - t(n-1)_{max}, t(n)_{min} - t(n-1)_{min}$) satisfies the following equation 1 to thereby diagnose whether cracking has occurred. If the calculated interline movement time is between the first reference value $$\left(\frac{Dn}{Vc} - \beta\right)$$

and the second reference value $$\left(\frac{Dn}{Vc} + \beta\right),$$

it is determined that cracking has occurred.

$$\frac{Dn}{Vc} - \beta \leq t(n)_{max} - t(n-1)_{max} \leq \frac{Dn}{Vc} + \beta \qquad \text{Equation 1}$$

$$\frac{Dn}{Vc} - \beta \leq t(n)_{min} - t(n-1)_{min} \leq \frac{Dn}{Vc} + \beta$$

wherein Dn is the distance between the temperature sensors in the n line and the temperature sensors in the n−1 line; VC is casting velocity; t(n)max is the time corresponding to the maximum temperature ($T_{max}$) immediately before the temperature of the n line decreases; t(n−1)max is the time corresponding to the maximum temperature ($T_{max}$) immediately before the temperature of the n−1 line decreases; t(n)min is the time corresponding to the minimum temperature ($T_{min}$) after the temperature of the n line has decreased;

t(n−1)min is the time corresponding to the minimum temperature ($T_{min}$) after the temperature of the n−1 line has decreased; and β is a set offset time.

Herein, the movement speed of continuously cast steel in the mold is at least about 15 cm per 10 sec, and the offset time may be set in the range from 1 sec to 2 sec. If the casting velocity is higher than 0.9 m/min or the interline spacing of the temperature sensors 11 changes, the offset time may be increased or decreased.

Figure 40:
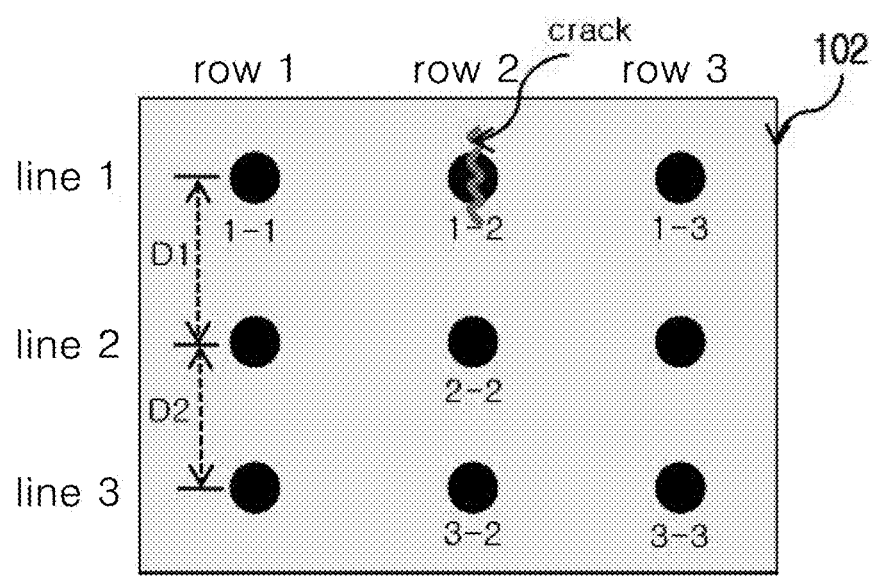
FIGS. 40 to 42 illustrate the movement of cracks in a mold.
Figure 41:
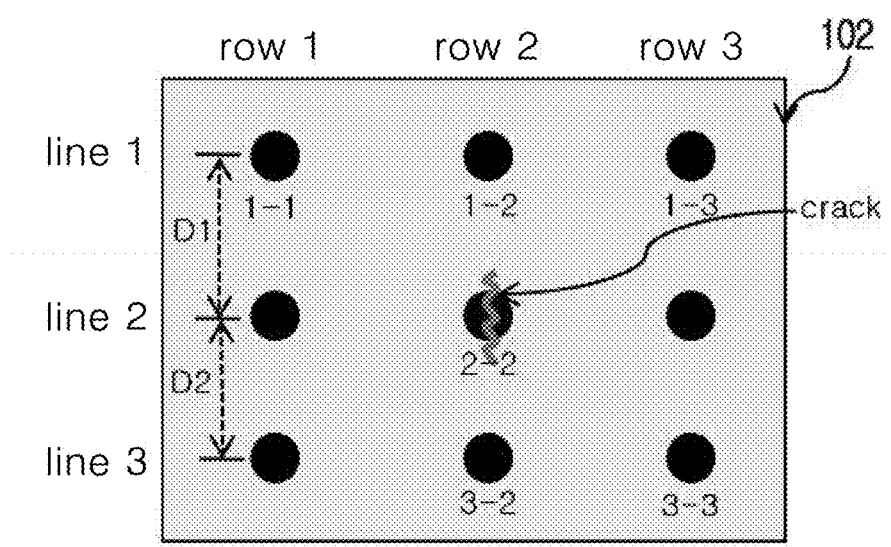
Figure 42:
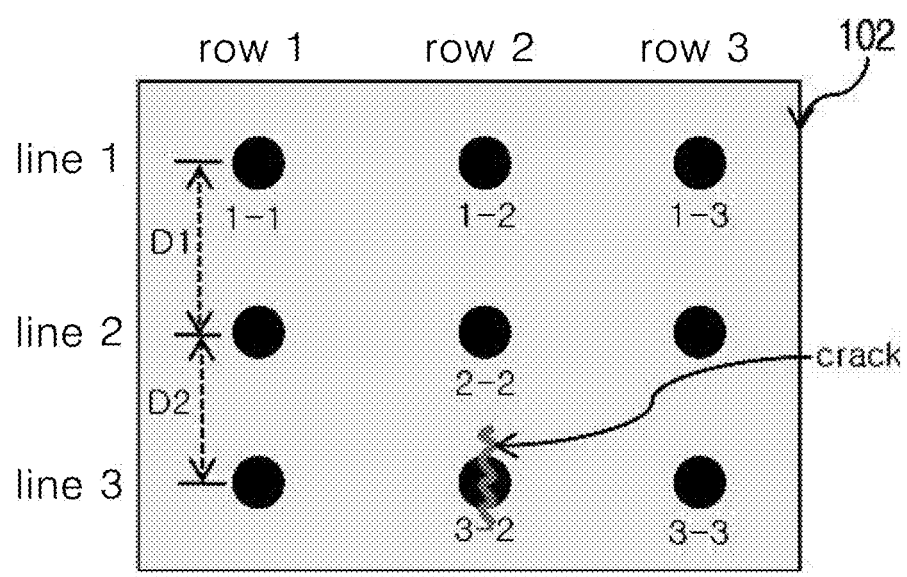

FIGS. 40 to 42 show that cracking has occurred in row 2. As shown in FIG. 40, cracking has occurred at a position corresponding to a temperature sensors 1-2 located in row 2 of line 1, and as shown in FIGS. 41 and 42, the generated cracks move to a temperature sensors 2-2 in row 2 of line 2 and a temperature sensors 3-2 in row 2 of line 3 with the passage of time.

Figure 43:
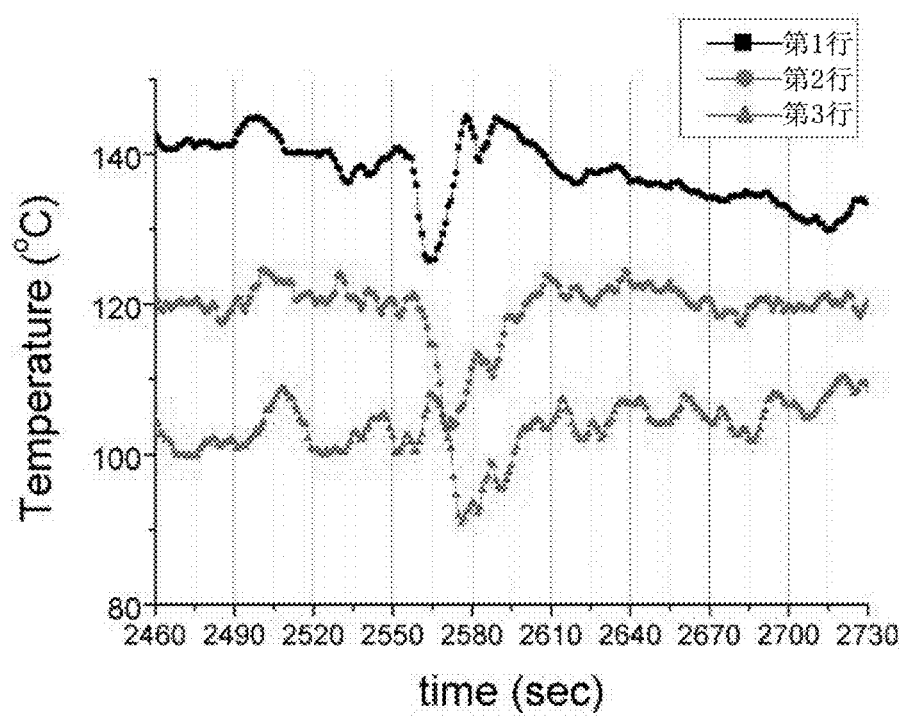
FIG. 43 is a graphic diagram showing the temperatures, measured by temperature sensor unit of the same row when cracking has occurred, as a function of time.

If cracking occurs in row 2 of line 1, as shown in FIG. 43, the temperature difference (between the maximum temperature ($T_{max}$) immediately before the temperature decreases and the minimum temperature ($T_{min}$) after the temperature has decreased) acquired by the temperature sensors in row 2 of line 1 will also continuously appear at the temperature sensors 2-2 in row 2 of line 2 and the temperature sensors 3-2 in row 2 of line 3 with the passage of time.

Whether cracking has occurred is diagnosed by determining whether the calculated interline movement time satisfies the reference conditions of the following equation 2. If the calculated interline movement time ($t(2)_{max}-t(1)_{max}$, $t(2)_{min}-t(1)_{min}$, $t(3)_{max}-t(2)_{max}$, $t(3)_{min}-t(2)_{min}$) is between the first reference value $$\left(\frac{D1}{Vc} - \beta \text{ or } \frac{D2}{Vc} - \beta\right)$$

or the second reference value $$\left(\frac{D1}{Vc} + \beta \text{ or } \frac{D2}{Vc} + \beta\right),$$

it is diagnosed that cracking has occurred.

$$\frac{D1}{Vc} - \beta \leq t(2)_{max} - t(1)_{max} \leq \frac{d1}{Vc} + \beta \quad \text{Equation 2}$$

$$\frac{D1}{Vc} - \beta \leq t(2)_{min} - t(1)_{min} \leq \frac{d1}{Vc} + \beta$$

$$\frac{D2}{Vc} - \beta \leq t(3)_{max} - t(2)_{max} \leq \frac{d2}{Vc} + \beta$$

$$\frac{D2}{Vc} - \beta \leq t(3)_{min} - t(2)_{min} \leq \frac{d2}{Vc} + \beta$$

wherein D1 is the distance between the temperature sensors in line 1 and the temperature sensors in line 2; D2 is the distance between the temperature sensors in line 2 and the temperature sensors in line 3; Vc is casting velocity; t(1)max is the time corresponding to the maximum temperature ($T_{max}$) immediately before the temperature of line 1 decreases; t(2)max is the time corresponding to the maximum temperature ($T_{max}$) immediately before the temperature of line 2 decreases; t(3)max is the time corresponding to the maximum temperature ($T_{max}$) immediately before the temperature of line 3 decreases; t(1)min is the time corresponding to the minimum temperature ($T_{min}$) after the temperature of line 1 has decreased; t(2)min is the time corresponding to the minimum temperature ($T_{min}$) after the temperature of line 2 has decreased; t(3)min is the time corresponding to the minimum temperature ($T_{min}$) after the temperature of line 3 has decreased; and β is a set offset time.

Thus, if the temperature difference between the maximum temperature ($T_{max}$) immediately before the temperature of each of the temperature sensors 111 and the minimum temperature ($T_{min}$) after the temperature has decreased is greater than the reference value and satisfies the reference conditions of the above equation 2, the processor 190 diagnoses that cracking has occurred in the relevant row.

This crack diagnosis algorithm considers the movement of cracks and shows relatively excellent performance for detecting small cracks which occur in a position corresponding to any temperature sensors and move to other lines with the passage of time as shown in FIGS. 40 to 42.

As described above, in the present invention, longitudinal cracks are diagnosed based on the variation in temperature and the movement time of a solidified shell that is produced in a continuous casting process, so that only the surface of a slab in which longitudinal cracks have occurred can be scarfed, thus reducing the cost for correcting slabs.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An apparatus for diagnosing cracking in a solidified shell in a mold, the apparatus comprising:
    a differential calculator configured to calculate a maximum temperature difference between an average temperature of a first group and an average temperature of each row of a second group based on the temperatures detected by a plurality of temperature sensors, wherein the plurality of temperature sensors are arranged in a matrix form in the mold, and the plurality of temperature sensors are divided into the first group and the second group based on a portion in which cracking is suspected to occur; wherein the temperature sensors in the first group are disposed on both edges of the mold, the temperature sensors in the second group are disposed in a central portion of the mold, at each side of the central vertical line of the mold, which is an area corresponding to 15% or less of the width of the mold; and
    a crack determinator configured to determine whether cracking has occurred in the solidified shell discharged from the mold using the calculated maximum temperature difference.

2. The apparatus of claim 1, wherein the first group comprises at least one temperature sensor disposed where no cracking occurs, and the second group comprises at least one temperature sensor disposed where cracking occurs.

3. The apparatus of claim 1, wherein the crack determinator is further configured to:
    compare the calculated temperature difference with a set reference value to determine whether cracking has occurred in the solidified shell.

4. The apparatus of claim 1, wherein the crack determinator is further configured to:
    determine whether cracking has occurred in the solidified shell using the temperature difference between an average temperature value of the first group and an average temperature value of the second group.

5. The apparatus of claim 1, wherein the crack determinator is further configured to:
   determine whether cracking has occurred in the solidified shell using the temperature difference between an average temperature value of the first group and an average temperature value of temperature sensors other than any one of the temperature sensors of the second group.

6. An apparatus for diagnosing cracking in a solidified shell in a mold, the apparatus comprising:
   a temperature sensor unit detecting temperatures of the mold using a first group of temperature sensors arranged in a central portion of the mold, in which cracking is suspected to occur; wherein the temperature sensor unit has a second group of sensors, and the second group of sensors are disposed on both edges of the mold, the temperature sensors in the first group are disposed it each side of a central vertical line of the mold, which is an area corresponding to 15% or less of the width of the mold; a differential calculator collecting the temperatures of the mold using the plurality of temperature sensors for a predetermined amount of time, calculating, from the collected mold temperatures, a temperature difference between a maximum temperature measured before the temperature of each temperature sensor decreases and a minimum temperature measured after the temperature has decreased; and a reference-value comparison unit configured to store, in a memory, the maximum temperature and the minimum temperature of each temperature sensor when the calculated temperature difference is greater than a reference value,
   a crack determinator configured to determine whether cracking has occurred in the solidified shell using the temperature of each temperature sensor disposed in a same row of the matrix,
   wherein the crack determinator calculates an interline movement time of the temperature difference using the temperature of the temperature sensors disposed in the same row of a matrix, and determines whether the calculated movement time is within a set reference condition range to determine whether cracking has occurred in the solidified shell.

7. The apparatus of claim 6, wherein the crack determinator is further configured to:
   compare the maximum temperature difference among the calculated temperature differences with a preset reference value to determine whether cracking has occurred in the solidified shell.

8. An apparatus for diagnosing cracking in a solidified shell in a mold, the apparatus comprising:
   a differential calculator configured to calculate an average temperature of a first group and an average temperature of each row of a second group, wherein a plurality of temperature sensors are arranged in a matrix form in the mold and divided into the first group and the second group based on a portion in which cracking is suspected to occur, and extract a maximum temperature difference and a minimum temperature difference between the calculated average temperature of the first group and the calculated average temperature of each row of the second group, wherein the temperature sensors in the first group are disposed on both edges of the mold, the temperature sensors in the second group are disposed in a central portion of the mold, at each side of the central vertical line of the mold, which is an area corresponding to 15% or less of the width of the mold; and
   a crack determinator configured to determine whether cracking has occurred in the solidified shell using the extracted maximum temperature difference and minimum temperature difference.

* * * * *